US010245206B2

(12) United States Patent
Dirks et al.

(10) Patent No.: US 10,245,206 B2
(45) Date of Patent: Apr. 2, 2019

(54) PNEUMATIC SOMATOSENSORY STIMULATION DEVICE AND METHOD

(71) Applicant: Epic Medical Concepts & Innovations, Inc., Mission, KS (US)

(72) Inventors: Aaron J. Dirks, Overland Park, KS (US); James R. Lucas, Prairie Village, KS (US)

(73) Assignee: Epic Medical Concepts & Innovations, Inc., Mission, KS (US)

( * ) Notice: Subject to any disclaimer, the term of this patent is extended or adjusted under 35 U.S.C. 154(b) by 1179 days.

(21) Appl. No.: 14/537,718

(22) Filed: Nov. 10, 2014

(65) Prior Publication Data

US 2015/0133830 A1 May 14, 2015

Related U.S. Application Data

(60) Provisional application No. 61/904,097, filed on Nov. 14, 2013.

(51) Int. Cl.
| | |
|---|---|
| *A61H 9/00* | (2006.01) |
| *A61B 5/00* | (2006.01) |
| *A61B 18/00* | (2006.01) |

(52) U.S. Cl.
CPC ......... *A61H 9/0057* (2013.01); *A61B 5/0053* (2013.01); *A61B 5/4005* (2013.01); *A61H 9/0007* (2013.01); *A61H 9/0071* (2013.01); *A61B 5/442* (2013.01); *A61B 2018/0088* (2013.01); *A61H 2201/5002* (2013.01); *A61H 2201/5071* (2013.01)

(58) Field of Classification Search
CPC .. A61B 2018/00434; A61B 17/320068; A61B 5/04001; G05B 2219/40568

USPC ............... 600/552; 340/407.1; 601/9, 46
See application file for complete search history.

(56) References Cited

U.S. PATENT DOCUMENTS

| | | | |
|---|---|---|---|
| 15,568 | A | 8/1856 | McLean |
| 655,747 | A | 8/1900 | Winckfield |
| 714,342 | A | 11/1902 | Watson |

(Continued)

FOREIGN PATENT DOCUMENTS

| | | |
|---|---|---|
| CN | 101065092 | 10/2007 |
| EP | 0538873 B1 | 9/1998 |

(Continued)

OTHER PUBLICATIONS

International Search Report & Written Opinion for PCT/US2014/064867, dated Feb. 26, 2015, 13 pages.

(Continued)

*Primary Examiner* — May A Abouelela
(74) *Attorney, Agent, or Firm* — Hovey Williams LLP

(57) ABSTRACT

A device for providing tactile stimulation of a subject via a pulse of compressible fluid, typically for medical diagnostic and therapeutic applications. The device preferably includes a high pressure fluid source and a low pressure fluid source. A pressure valve selectively connects the pressure sources to an outlet conduit. The outlet conduit includes an applicator for directing pulses against the skin of a subject. The pulses may be applied via one applicator or a plurality of applicators, and may be applied in one pattern or several patterns at various application sites. A method of providing tactile stimulation is also disclosed.

22 Claims, 11 Drawing Sheets

(56) References Cited

U.S. PATENT DOCUMENTS

| | | | |
|---|---|---|---|
| 841,146 A | 1/1907 | Hasbrouck | |
| 882,532 A | 3/1908 | McCall | |
| 907,749 A | 12/1908 | Davenport | |
| 931,102 A | 8/1909 | Walter | |
| 939,822 A | 11/1909 | Fey | |
| 1,179,129 A | 4/1916 | Maxam | |
| 1,212,845 A | 1/1917 | Talley | |
| 1,217,886 A | 2/1917 | Hopkins | |
| 1,858,209 A | 5/1927 | Lang | |
| 1,714,898 A | 5/1929 | Zund-Burguet | |
| 1,805,675 A | 1/1930 | Rudolph | |
| 1,858,652 A | 5/1932 | Wigle | |
| 1,882,040 A | 10/1932 | Roehm | |
| 2,234,102 A | 4/1937 | Andres | |
| 2,087,491 A | 7/1937 | Whitehurst | |
| 2,234,101 A | 3/1941 | Andres | |
| 2,266,931 A | 12/1941 | Wheeler | |
| 2,295,817 A | 9/1942 | Winther | |
| 3,236,231 A | 2/1966 | Schneider | |
| 3,315,665 A | 4/1967 | MacLeod | |
| 3,403,673 A | 10/1968 | MacLeod | |
| 3,763,854 A | 10/1973 | Welch | |
| 3,841,322 A | 10/1974 | Spelio | |
| 3,910,262 A | 10/1975 | Stoughton | |
| 4,003,373 A | 1/1977 | Spelio | |
| 4,428,368 A | 1/1984 | Torii | |
| 4,577,626 A | 3/1986 | Marukawa | |
| 4,836,192 A | 6/1989 | Abbate | |
| 4,941,458 A | 7/1990 | Taheri | |
| 5,035,016 A | 7/1991 | Mori | |
| 5,220,921 A | 6/1993 | Ferris | |
| 5,228,431 A * | 7/1993 | Giarretto | A61H 9/005 601/11 |
| 5,377,702 A | 1/1995 | Sakurai | |
| 5,800,397 A | 9/1998 | Wilson | |
| 6,182,658 B1 | 2/2001 | Hayek | |
| 6,450,981 B1 | 9/2002 | Shabty et al. | |
| 6,609,035 B1 | 8/2003 | Liska | |
| 6,708,691 B1 | 3/2004 | Hayek | |
| 6,757,916 B2 * | 7/2004 | Mah | B64D 10/00 2/2.14 |
| 6,823,678 B1 * | 11/2004 | Li | A41D 13/0025 62/259.3 |
| 6,990,377 B2 | 1/2006 | Gliner et al. | |
| 8,235,920 B2 | 8/2012 | Biggie et al. | |
| 8,273,039 B1 * | 9/2012 | Ignagni | A61H 9/0078 601/150 |
| 8,460,223 B2 | 6/2013 | Huster et al. | |
| 2001/0031911 A1 | 10/2001 | Khouri | |
| 2002/0042585 A1 * | 4/2002 | Kloecker | A61F 5/34 602/13 |
| 2003/0069528 A1 | 4/2003 | Herz et al. | |
| 2003/0216672 A1 | 11/2003 | Rastegar et al. | |
| 2003/0216692 A1 | 11/2003 | Fago et al. | |
| 2003/0236456 A1 | 12/2003 | Graham et al. | |
| 2004/0260218 A1 | 12/2004 | Shah et al. | |
| 2005/0070405 A1 | 3/2005 | Egger | |
| 2005/0235988 A1 | 10/2005 | Hansen et al. | |
| 2005/0270029 A1 | 12/2005 | Ehman et al. | |
| 2006/0206040 A1 | 9/2006 | Greenberg | |
| 2006/0211958 A1 | 9/2006 | Rosenberg et al. | |
| 2006/0236456 A1 | 10/2006 | Beale | |
| 2007/0100263 A1 | 5/2007 | Merfeld | |
| 2007/0212335 A1 | 9/2007 | Hantash et al. | |
| 2008/0064994 A1 | 3/2008 | Guantera et al. | |
| 2008/0069895 A1 | 3/2008 | Liu et al. | |
| 2008/0091126 A1 | 4/2008 | Greenberg | |
| 2008/0095748 A1 | 4/2008 | Kharazi et al. | |
| 2008/0132816 A1 | 6/2008 | Kane et al. | |
| 2009/0012434 A1 | 1/2009 | Anderson | |
| 2009/0210026 A1 | 8/2009 | Solberg et al. | |
| 2009/0250071 A1 | 10/2009 | Kimani Mwangi | |
| 2010/0010400 A1 | 1/2010 | Martin et al. | |
| 2010/0030120 A1 | 2/2010 | Graham et al. | |
| 2010/0100017 A1 | 4/2010 | Maguina | |
| 2011/0196269 A1 | 8/2011 | Arkans | |
| 2012/0053483 A1 | 3/2012 | Doidge et al. | |
| 2012/0109029 A1 | 5/2012 | Ma | |
| 2012/0157895 A1 | 6/2012 | Barlow et al. | |
| 2014/0197937 A1 * | 7/2014 | Huang | A61H 9/0071 340/407.1 |

FOREIGN PATENT DOCUMENTS

| | | |
|---|---|---|
| EP | 2371274 A1 | 10/2011 |
| JP | 2007-500053 | 1/2007 |
| JP | 2008-093286 | 4/2008 |
| JP | 2009-034404 | 2/2009 |
| JP | 2013-503002 | 1/2013 |
| WO | 2011107860 A1 | 9/2011 |
| WO | 2013025823 A2 | 2/2013 |
| WO | 2014145914 A1 | 9/2014 |

OTHER PUBLICATIONS

Hammer, Michael J., Design of a New Somatosensory Stimulus Delivery Device for Measuring Laryngeal Mechanosensory Detection Thresholds in Humans, National Institute of Health (NIH) Public Access Author Manuscript, IEEE Trans Biomed Eng., Apr. 2009, 16 pages, vol. 56 (4), USA.

Nunziata, Enrico, Effect of Tactile Stimulation Pulse Characteristics on Sensation Threshold and Power Consumption, Maxwell Pergamon Macmillan plc, Annals of Biomedical Engineering, vol. 17, pp. 423-435, 1989, USA.

FOI Services, 5246135—A [K913604]: Biomagnetic Technologies 510 (k): Somatosensory Stimulus System, dated Jul. 25, 2012, 132 pages.

Wienbruch et al., A portable and low-cost fMRI compatible pneumatic system for the investigation of the sompatosensory system in clinical and research environments, Neuroscience Letters 398 (2006), pp. 183-188.

Briggs, R.W., Dy-Liacco, I., Malcom, M.P., Lee, H., Peck, K.K., Gopinath, K.S., Himes, N.C., Soltysik, D.A., Browne, P. and Tran-Son-Tay, R. (2004), A Pneumatic Vibrotactile Stimulation Device for fMRI. Magn Reson Med, 51: 640-643. doi: 10.1002/mrm.10732.

Huang, R.S., Sereno, M., Dodecapus: An MR-compatible system for somatosensory, NeuroImage (2006), doi: 10.1016/j.neuroimage.2006.10.24, http://www.ncbi.nlm.nih.gov/pubmed/17182259.

* cited by examiner

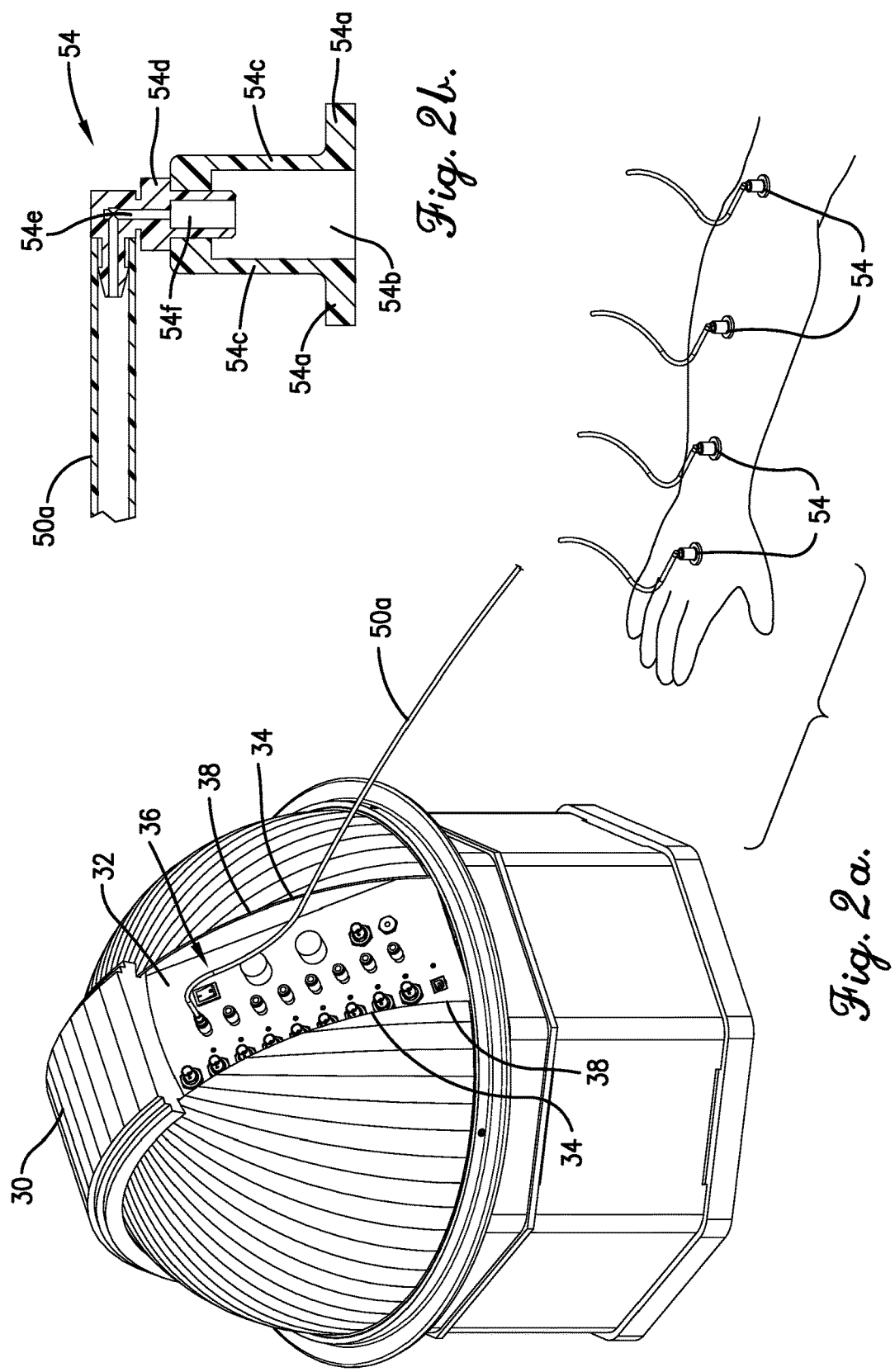

PNEUMATIC SOMATOSENSORY STIMULATION DEVICE AND METHOD

RELATED APPLICATION

This application claims the benefit of U.S. Provisional Application Ser. No. 61/904,097, filed Nov. 14, 2013, entitled PNEUMATIC SOMATOSENSORY STIMULATION DEVICE, which is hereby incorporated in its entirety by reference herein.

BACKGROUND OF THE INVENTION

1. Field of the Invention

The present invention relates to apparatuses and methods for tactile stimulation. The present invention more particularly relates to a pneumatic device and method for tactile stimulation using pulses of compressible fluid.

2. Discussion of the Prior Art

Tactile stimulation devices operate by inducing activation of the nerve endings and receptors proximate to a subject's skin, commonly either by applying electrical voltage to, or by mechanically stimulating, the surface of the skin. Once a neuron is activated, normal operation involves firing a signal along a neuronal path to the brain where the sensory input signal is ultimately interpreted, for example as a simulated puff or tap.

Tactile stimulation has a number of uses, primarily in the medical field, which include testing and diagnosis as well as therapeutic applications. For example, it is common to correlate tactile stimuli with brain activity to determine whether a neuronal path and/or the brain are functioning properly, such as in stroke victims, and/or to provide therapy using patterns of tactile stimulation. Where brain activity is recorded in response to tactile stimuli, it is typically detected using functional magnetic resonance imaging (fMRI), magnetoencephalography scanning (MEG), or the like. Subjects' physical responses elicited by tactile stimulation devices, such as reflexive movements, may also or alternatively be measured. Additional information on somatosensory stimulation and its applications can be found in U.S. Publication No. 2012/0157895 A1 (Barlow et al.), which is hereby incorporated by reference in its entirety.

It is common to refer to a graph of stimulus levels (whether stimulus levels are measured by amplitude in volts, pressure/force or other units) over time as a "waveform," with such stimulus levels being susceptible of measurement at a variety of locations but most commonly at an application site. Different pulse waveforms, for example rectangles or parabolas, and frequencies are desirable for different applications and objectives.

Known tactile stimulation devices that rely on electrical current to carry pulses that induce neuronal signal firing typically do so by driving current to an application site where it is either applied to the skin directly via an electrode or the like, or where it is used to actuate a physical intermediary that translates the current into mechanical motion and contact with the subject. An example of the latter type is a coil wrapped around a cylinder, where the current-bearing coil interacts with an existing magnetic field to induce movement of the cylinder toward the skin of a subject. Electrical current tactile stimulation devices suffer from shortcomings which include the possibility of interference with brain activity measurements and discomfort for the subjects, and difficulty attributing brain activity measurements to bodily responses rather than the stimulation device and its pulse(s).

Known tactile stimulation devices that rely on air as a pulse transfer medium typically comprise a compressor motor for supplying pulses of air to a line directed toward an application site of a subject. Such devices are generally configured so that the compressor motor may be turned on and off to create pressurized pulses at a given frequency for delivery along the line to the application site. Stimulation by these devices may either be effected by direct expulsion of the air pulses onto the subject's skin or other sensory surface (such as the throat) or by an air-actuated physical intermediary affixed to the skin, such as a simple retractable cylinder, that directly translates at least some of the force of the air pulses into mechanical contact with the skin.

Tactile stimulation devices relying on air for delivery of pulses to a subject suffer from a number of shortcomings, including sluggish pulse rise time and imprecise waveforms. It is known to attempt to correct for these shortcomings in applications where pulses travel over relatively long tube passages such as ten to twenty feet by locating a chamber holding compressed air to supply the pulses closer to the application site of the subject. However, such designs may involve increased complexity and cost, and the undesirable placement of additional equipment in "clean" rooms in which measurements are being taken. It is therefore desirable to provide an improved pneumatic device and method for tactile stimulation using pulses of compressible fluid.

This background discussion is intended to provide information related to the present invention which is not necessarily prior art.

SUMMARY

Embodiments of the present invention solve the above-described and other problems and limitations by providing an improved tactile stimulation using a pneumatic device for delivering pulses of compressible fluid over a distance so that sluggish rise time, imprecise waveforms and other disadvantages of existing pneumatic tactile stimulation devices can be minimized. In one implementation, the present invention accomplishes this with a less complex and less expensive solution that does not, for example, require positioning of pressure sources that are likely to interfere with sensory equipment operation.

According to one aspect of the present invention, a tactile stimulation device includes a high pressure fluid source, a low pressure fluid source, and an outlet conduit being fluidly connectable to the fluid sources and including an applicator configured to direct a pulse against the skin of a subject. The device further includes a pressure valve fluidly interposed between the applicator and the fluid sources. The pressure valve is shiftable between a high pressure position, in which the high pressure fluid source is fluidly connected to the outlet conduit, and a low pressure position, in which the low pressure fluid source is fluidly connected to the outlet conduit. Positioning of the pressure valve in the high pressure position and the low pressure position supplies the pulse of compressible fluid to the applicator.

A second aspect of the present invention concerns a device for providing tactile stimulation via a pulse of compressible fluid. The device includes a pressurized fluid source operable to generate the pulse of compressible fluid, a vacuum pressure source, and an outlet conduit fluidly connectable to the sources and including an applicator configured to direct the pulse against the skin of a subject. The device further includes a vacuum valve shiftable between a vacuum position, in which the vacuum pressure source is fluidly connected to the outlet conduit, and a pulse position, in which the vacuum pressure source is not fluidly connected to the outlet conduit. The vacuum valve shifting from the vacuum position to the pulse position permits the pulse of compressible fluid to propagate toward the applicator.

In regard to a third aspect of the present invention, a tactile stimulation method is provided. The method includes the steps of supplying a high pressure compressible fluid toward an applicator, and, after passage of a first predetermined amount of time, switching the flow of high pressure fluid to a flow of low pressure compressible fluid toward the first applicator. According to this embodiment, the high pressure fluid flows for less time than the low pressure fluid to generate the pulse of compressible fluid to the first applicator.

This summary is provided to introduce a selection of concepts in a simplified form. These concepts are further described below in the detailed description of the preferred embodiments.

This summary is not intended to identify key features or essential features of the claimed subject matter, nor is it intended to be used to limit the scope of the claimed subject matter.

Various other aspects and advantages of the present invention will be apparent from the following detailed description of the preferred embodiments and the accompanying drawing figures.

BRIEF DESCRIPTION OF THE DRAWING FIGURES

Preferred embodiments of the present invention are described in detail below with reference to the attached drawing figures, wherein:

FIG. 1b is a front perspective view of the device of FIG. 1a;

FIG. 2a is a front perspective view of the device of FIG. 1 with applicators applied to the arm of a subject, and depicting part of the outlet conduits associated with the applicators, with one of the conduits being shown connected to the control panel;

FIG. 2b is an enlarged cross-sectional side view of one of the applicators;

Figure 1A:
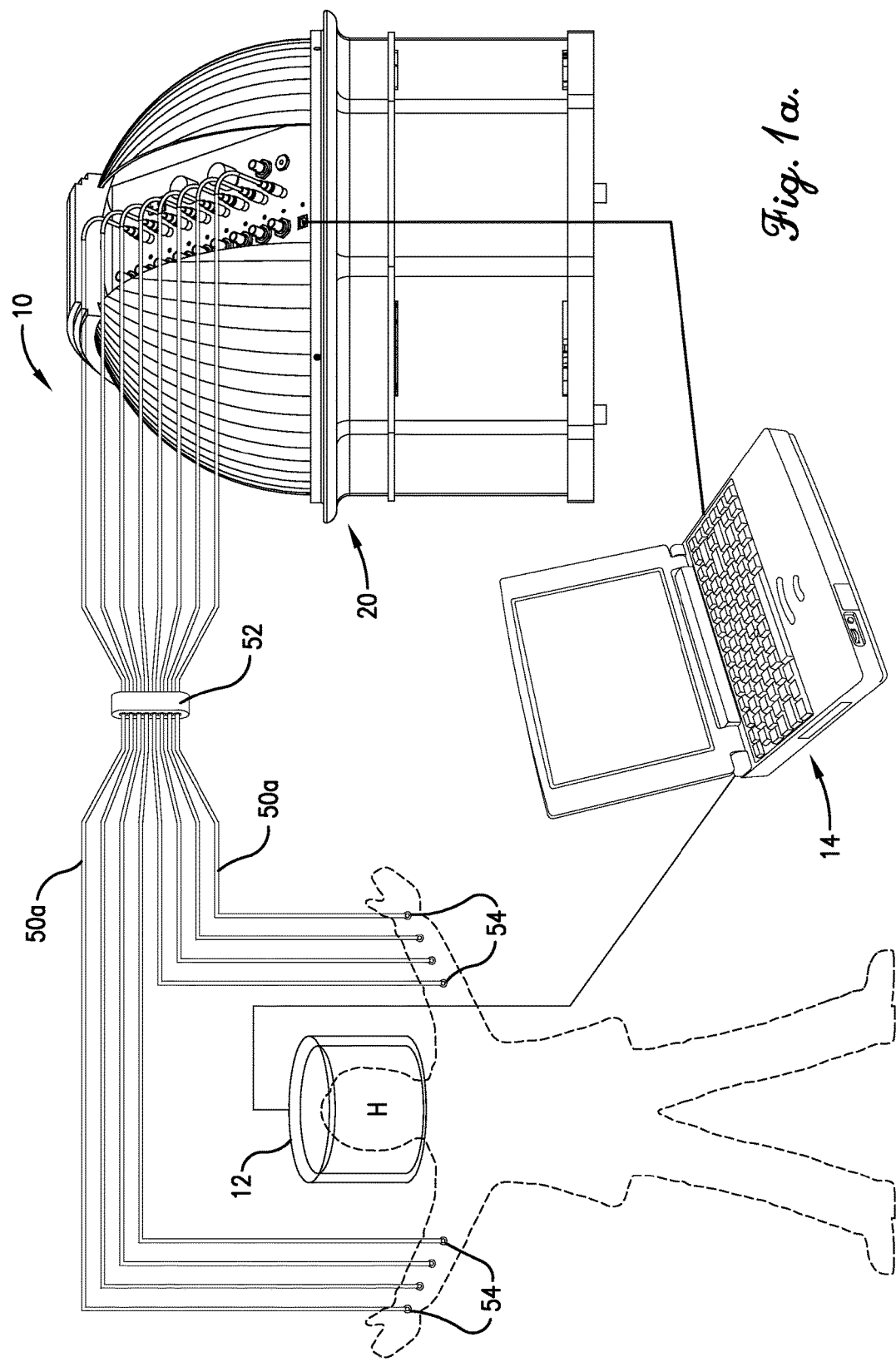
FIG. 1a is a front perspective view of a tactile stimulation device constructed in accordance with a first preferred embodiment of the present invention together with a sensing device.
Figure 1C:
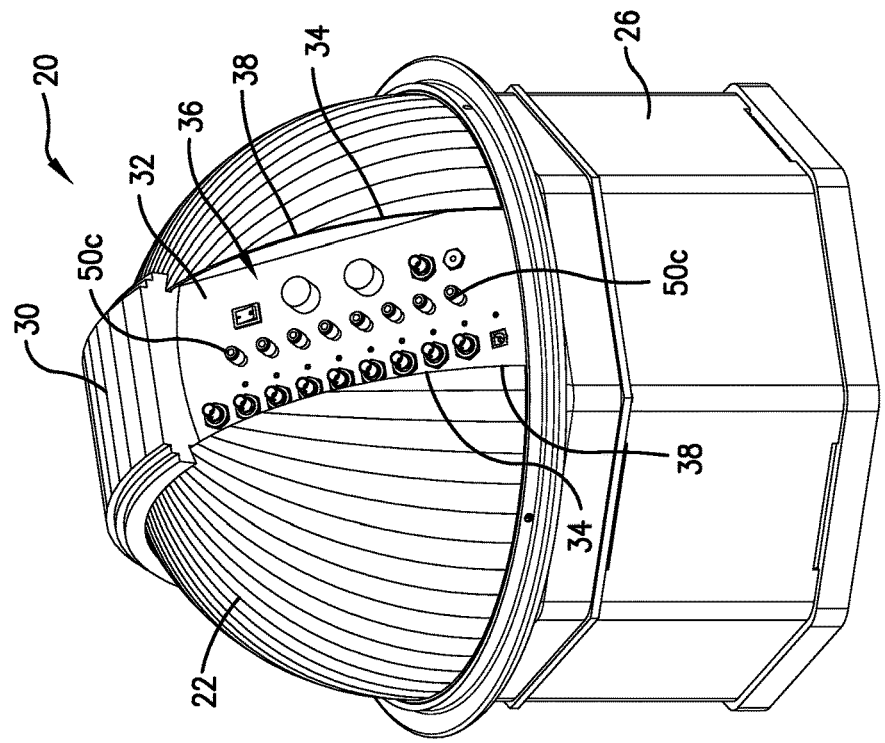
FIG. 1c is a front perspective view of the device of FIGS. 1a-b, illustrating the control panel cover in a retracted condition.
Figure 1B:
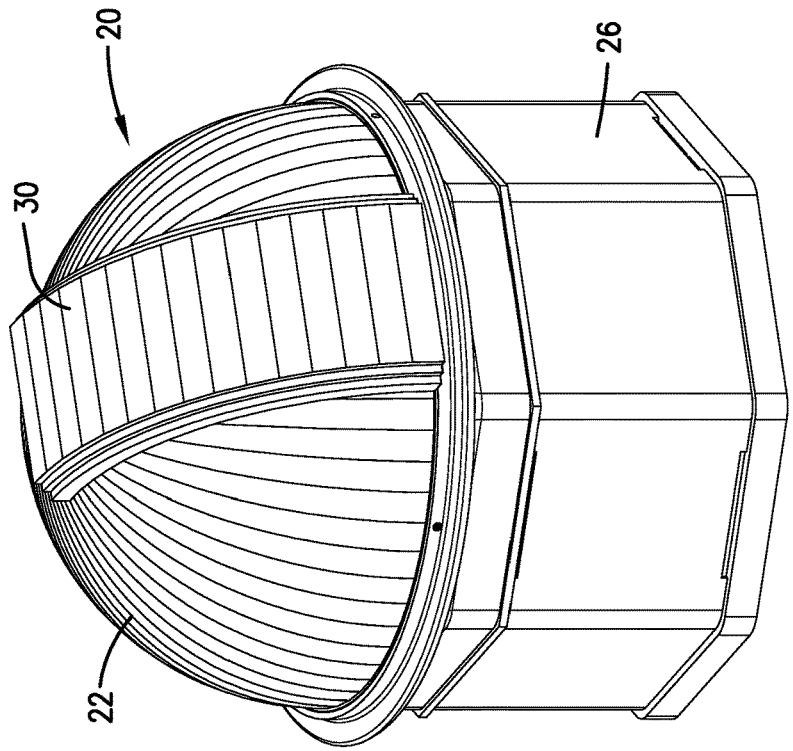
Figure 1D:
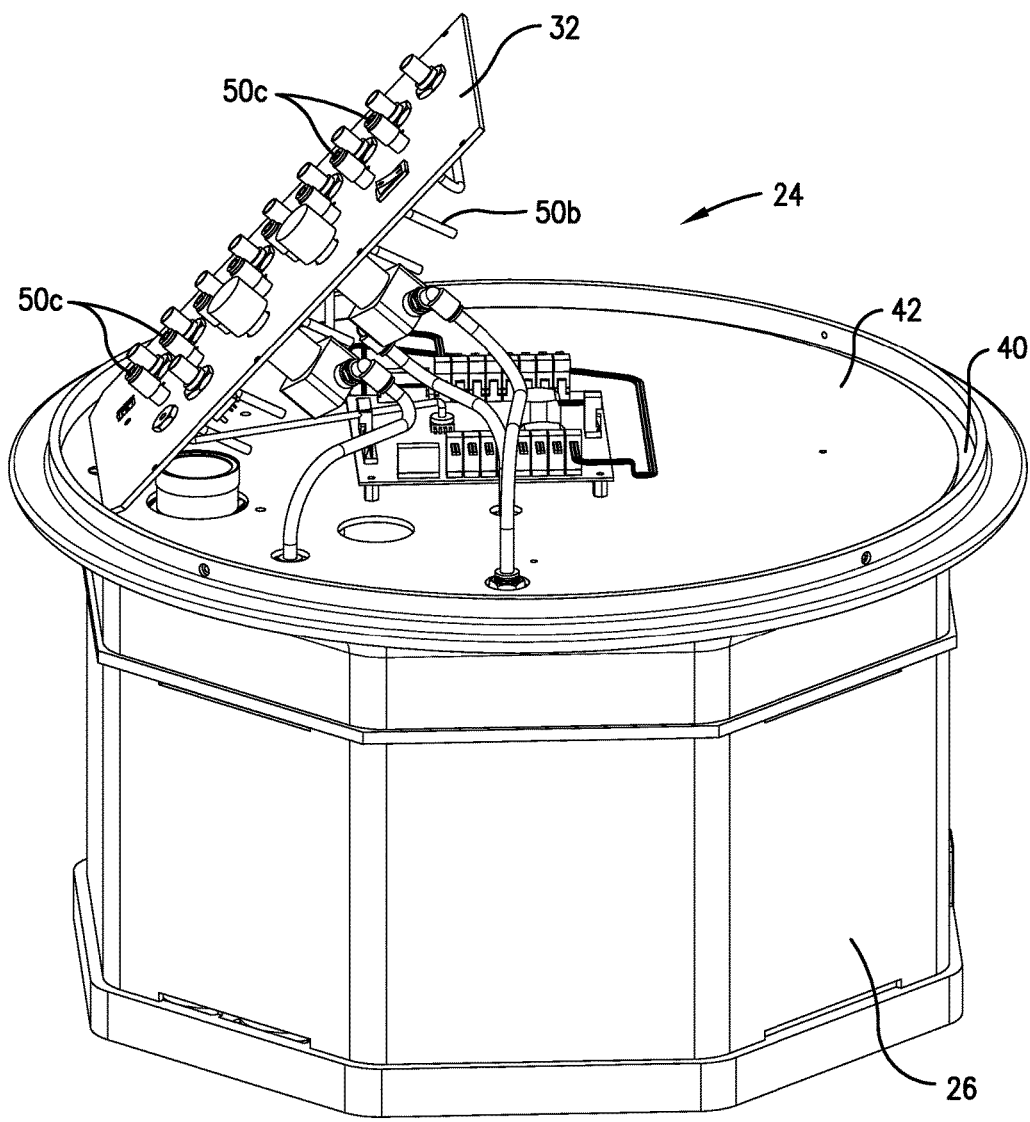
FIG. 1d is a partially sectioned elevated side perspective view of the device, with the upper section of the housing being removed to show the top compartment of the device of FIGS. 1a-c.

The drawing figures do not limit the present invention to the specific embodiments disclosed and described herein. The drawings are not necessarily to scale, emphasis instead being placed upon clearly illustrating the principles of the preferred embodiments.

Furthermore, directional references (e.g., top, bottom, front, back, up, down, etc.) are used herein solely for the sake of convenience and should be understood only in relation to each other. For instance, a component might in practice be oriented such that faces referred to as "top" and "bottom" are sideways, angled, inverted, etc. relative to the chosen frame of reference.

It is also noted that, as used herein, the terms axial, axially, and variations thereof mean the defined element has at least some directional component along or parallel to the axis. These terms should not be limited to mean that the element extends only or purely along or parallel to the axis. For example, the element may be oriented at a forty-five degree (45°) angle relative to the axis but, because the element extends at least in part along the axis, it should still be considered axial. Similarly, the terms radial, radially, and variations thereof shall be interpreted to mean the element has at least some directional component in the radial direction relative to the axis.

It is further noted that the term annular shall be interpreted to mean that the referenced object extends around a central opening so as to be generally toroidal or ring-shaped. It is not necessary for the object to be circular, nor does the object have to be continuous. Similarly, the term toroidal shall not be interpreted to mean that the object must be circular or continuous.

DETAILED DESCRIPTION OF THE PREFERRED EMBODIMENTS

The present invention is susceptible of embodiment in many different forms. While the drawings illustrate, and the specification describes, certain preferred embodiments of the invention, it is to be understood that such disclosure is by way of example only. There is no intent to limit the principles of the present invention to the particular disclosed embodiments.

In this description, references to "one embodiment", "an embodiment", or "embodiments" mean that the feature or features referred to are included in at least one embodiment of the invention. Separate references to "one embodiment", "an embodiment", or "embodiments" in this description do not necessarily refer to the same embodiment and are not mutually exclusive unless so stated. Specifically, a feature, structure, act, etc. described in one embodiment may also be included in other embodiments, but is not necessarily included. Thus, particular implementations of the present invention can include a variety of combinations and/or integrations of the embodiments described herein.

FIG. 1a illustrates a tactile stimulation device 10 and a generic sensing device 12 shown as a cylinder surrounding the head H of the subject, which may be a human or other animal having somatosensory receptors. The sensing device 12 may be used in certain embodiments to provide data to a computer 14 regarding the subject's reaction(s) to a pulse supplied by the tactile stimulation device 10. In the preferred embodiment, the computer 14 is also part of a control system of the tactile stimulation device 10, as discussed in further detail below. The sensing device 12 may include any of a variety of known equipment used for sensing neuronal activity in the brain or elsewhere in the nervous system of the body, such as fMRI or MEG equipment, and/or may include a mechanical, auditory or optical sensing device such as a motion sensor, microphone or camera, without departing from the spirit of the present invention.

Broadly characterized, embodiments of the present invention provide improved tactile stimulation using a pneumatic device for delivering pulses of compressible fluid over a distance so that sluggish rise time, imprecise waveforms and other disadvantages of existing pneumatic tactile stimulation devices can be minimized. In one implementation, the present invention accomplishes this with a less complex and less expensive solution that does not, for example, require positioning of pressure sources that are likely to interfere with sensory equipment operation.

Figure 3A:
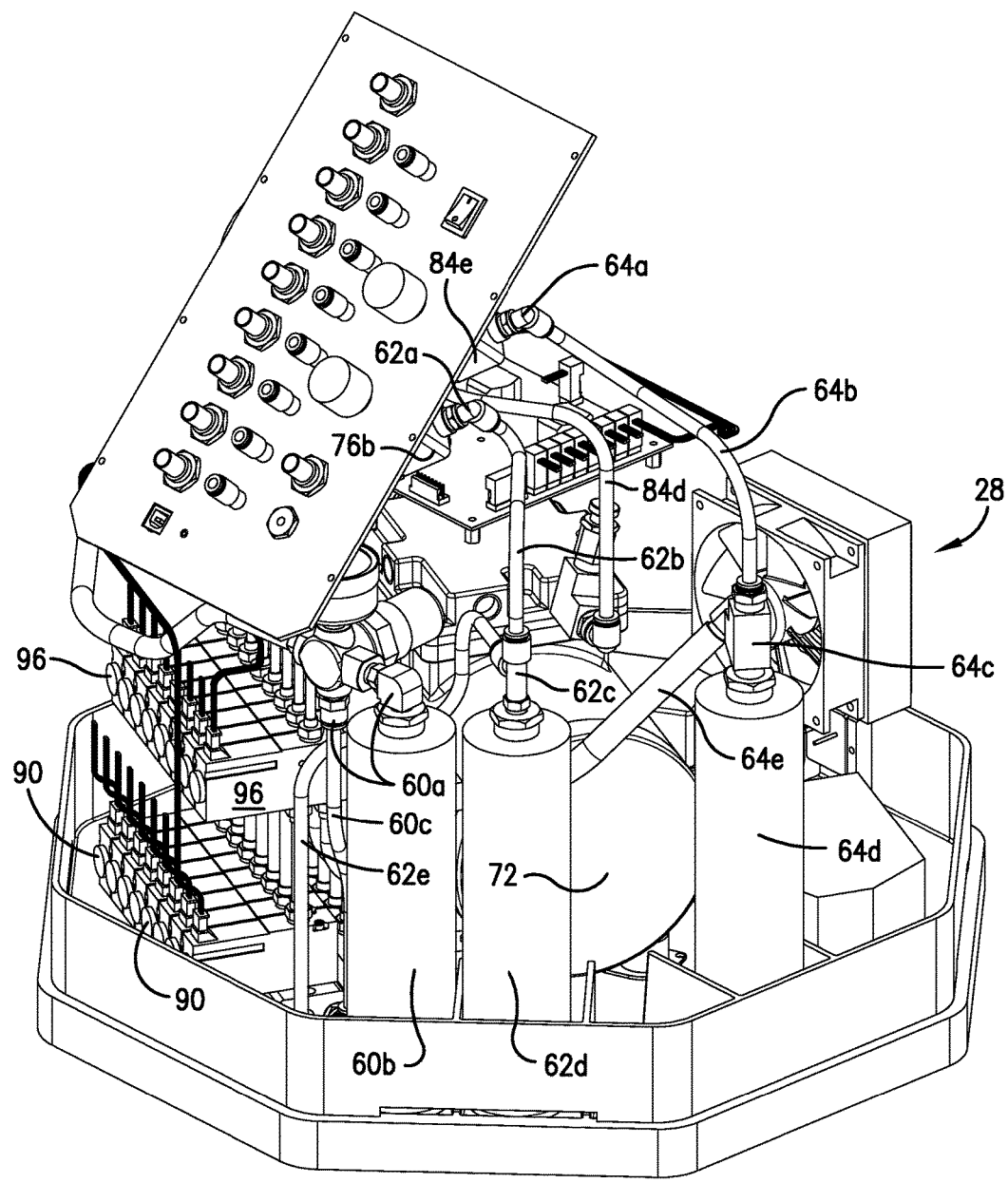
FIG. 3a is a partially sectioned perspective of the device of FIGS. 1 and 2, with the upper housing section and part of the lower housing section being removed to show the vacuum outlet side of the bottom compartment.
Figure 3B:
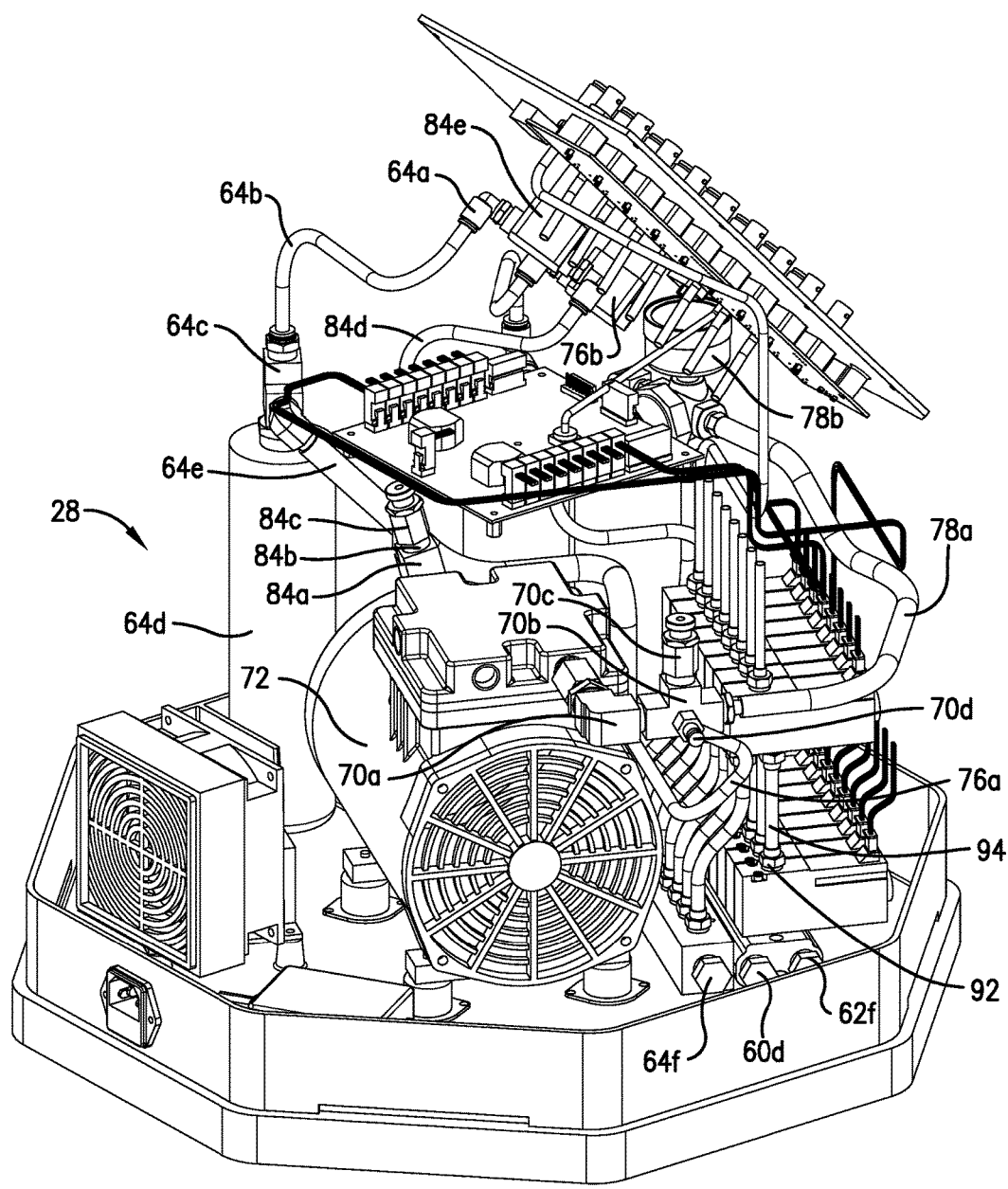
FIG. 3b is a partially sectioned perspective view of the device taken from the opposite angle of FIG. 3a to show the pressure outlet side of the bottom compartment.

Referring to the figures, a tactile stimulation device 10 constructed in accordance with a preferred embodiment of the present invention is shown. Referring to FIGS. 1a-d, the device 10 generally includes a mobile housing 20 having a dome upper section 22 defining an upper compartment 24 and an octagonal lower section 26 defining a lower compartment 28 (see FIG. 3a). The upper section 22 of the mobile housing 20 includes an arcuate control panel cover 30 for retractable covering of a control panel 32. The upper section 22 further includes a rectangular rim 34 defining a panel opening 36. The control panel 32 is fixed to an inner surface (not shown) of the rectangular rim 34. The rectangular rim 34 of the upper section 22 further defines bearing surfaces 38 along two sides of the panel opening 36 that receive the panel cover 30 and along which the panel cover 30 can slide to reveal or conceal the control panel 32.

The upper and lower sections 22, 26 of the mobile housing 20 may be separated by lifting the upper section 22 away from the lower 26. In alternative embodiments, the sections 22, 26 may be releasably fixed to each other by common releasable fasteners (not shown) such as clips or pins. An annular flange 40 (see FIG. 1d) extends from a top portion of the lower section 26 of the mobile housing 20, and the upper and lower compartments 24, 28 are separated by a substantially planar removable platform 42 supported on the flange 40. The mobile housing 20 provides supporting and transportable structure for many of the device's 10 components, while also providing reasonable access to such components for maintenance and tuning. The shape and configuration of the mobile housing 20 may be varied without departing from the principles of the present invention.

Turning now to FIGS. 1a-d and 2a, the device 10 preferably includes a plurality of outlet conduits 50. In the illustrated embodiment, the conduits 50 extend through the control panel 32 toward a subject. Preferably, the device includes a sleeve 52 for holding and directing the outlet conduits 50 over part of their initial proximate length (see FIG. 1a). Each conduit 50 preferably terminates in a distal applicator 54 affixed to the subject's skin. Each outlet conduit 50 includes an external section 50a that is outside the mobile housing 20, and an internal section 50b located inside the mobile housing 20. Preferably, each conduit 50 also includes a quick coupler 50c seated in the control panel 32. The quick coupler 50c releasably receives the corresponding external section 50a to establish fluid connection to the respective internal section 50b (see FIG. 1d). Each internal section 50b is secured to the internal side of the corresponding quick coupler 50c.

Each external section 50a preferably includes tube portions of different flexibility, with a portion of stiffer tube proximate to the mobile housing 20 being joined to a distal portion of more flexible tube nearer the subject. The portions may be integral, or may be coupled using common coupling structures (not shown) such as quick couplers or tubing clamps (i.e., perforated metal bands with screw fasteners). Another exemplary tube coupling structure may include a friction fit coupling head formed at the end of the stiffer tube portion. The coupling head may be configured for insertion into the end of the more flexible tube portion to complete the friction fit. It is envisioned that other coupling structures for joining the portions of each external section 50a may be used without departing from the spirit of the present invention.

During setup and operation, the stiffer tube portions of the external sections 50a may improve handling and positional retention of the external sections 50a as they extend from the mobile housing 20 toward a space near the subject, and the more flexible tube portions may provide for easier adjustment of the applicators 54 in the space near the subject so they may be fixed in desired application site pattern(s).

In a preferred embodiment, the outlet conduit 50 comprises plastic tubing such as urethane or silicone tubing or other materials having minimal magnetic responsiveness, with a minimum inner passageway cross-sectional dimension of between about 0.002 square inches and about 0.05 square inches.

The outlet conduit 50 also is preferably of a smooth bore to minimize pressure drop of the compressible fluid along its length. The external sections 50a of the outlet conduits 50 are preferably between about three (3) and about thirty (30) feet in length, and are about sixteen (16) feet in many commercial embodiments. However, it is envisioned that outlet conduits comprising different materials, dimensions and properties may be utilized in other embodiments without departing from the spirit of the present invention. For example, it is not required to have separate internal and external sections of the outlet conduit coupled by a quick coupler. The outlet conduit may alternatively be one continuous tube. Likewise, it is not required that the part of the outlet conduit that is outside the mobile housing comprise two portions, but could instead merely comprise one integral portion having uniform flexibility.

Turning now to FIG. 2b, an applicator 54 is illustrated at the distal end of each outlet conduit 50. The preferred applicator 54 is generally cylindrical, and includes an annular lip 54a extending radially outward from an interior space 54b defined by an inner surface of an applicator wall 54c. The annular lip 54a is configured to provide a sealing surface generally facing the subject that may be affixed to the subject's skin, for example using an adhesive or tape, to hold the applicator 54 against the skin. The seal may or may not be substantially complete, depending on the embodiment employed. The applicator 54 further includes a base 54d having an internal passage 54e for carrying pulses from the external section 50a into an entry chamber 54f of the base 54d. Pulses flowing from the external section 50a first flow through the base 54d at its internal passage 54e and then entry chamber 54f, and exit the base 54d into the interior space 54b. The pulses are then expelled onto the subject's skin to provide tactile stimuli.

The applicator 54 may, in alternative embodiments, include an applicator attachment such as a vibratory membrane or retractable cylinder for translating the pulses of compressible fluid into mechanical movement of the applicator attachment toward and into contact with the skin of the subject to achieve stimulation.

It is envisioned that the applicator may alternatively comprise different shapes, dimensions and flow paths without departing from the spirit of the present invention. For example, it is not required to have a distinct structure for delivering pulses to the skin of the subject, and a generic terminal end of an outlet conduit may alternatively be operable to fix against the subject's skin for delivery of pulses. By way of further example, applicators may vary in shape and dimension, including with respect to internal flow passageways and the presence or absence of internal chambers. An alternative applicator may further include rotatable or swiveling connections to tubing of the external portion of the outlet conduit, without departing from the spirit of the present invention.

Turning to FIGS. 3a-b and 4a-b, the device of the preferred embodiment is illustrated further including a high pressure fluid source 60, low pressure fluid source 62, and vacuum pressure source 64. In the illustrated preferred embodiment, high pressure fluid source 60 includes an upstream pressure supply 70 beginning at a compressor 72. Pressure supply 70 includes a compressor pressure outlet 70a (see FIG. 3b) and a T-connection 70b that includes a pressure release valve 70c. T-connection 70b also includes a needle valve 70d for regulating the flow of compressible fluid to a low pressure feed line 76a (see discussion of low pressure fluid source 62 below). Pressure release valve 70c is configured to open and release compressible fluid if the fluid pressure exceeds a threshold value, and to close once the compressible fluid pressure recedes below the threshold value. T-connection 70b is also fluidly connected to tube 78a, and tube 78a supplies compressible fluid to high pressure regulator 78b which, in turn, is fluidly connected and supplies compressible fluid at a high pressure to high pressure regulator outlets 60a. In a preferred embodiment, the high pressure regulator 78b supplies compressible fluid to high pressure regulator outlets 60a at between about six (6) psig and about ten (10) psig, and at about seven (7) psig for many commercial embodiments. High pressure regulator outlets 60a are fluidly connected to each other. High pressure regulator outlets 60a are also respectively fluidly connected to a high pressure reservoir 60b and a high pressure manifold inlet tube 60c. High pressure fluid source 60 further includes high pressure manifold 60d, which is fluidly connected to and supplied with compressible fluid by the high pressure manifold inlet tube 60c.

Low pressure fluid source 62 also includes upstream pressure supply 70 beginning at compressor 72 and including outlet 70a, t-connection 70b, release valve 70c and needle valve 70d. Needle valve 70d feeds line 76a. Line 76a is fluidly connected to low pressure reservoir 62d which, in turn, is fluidly connected via the components discussed below to low pressure regulator 76b. Low pressure regulator 76b is preferably a back pressure regulator, and is configured to release compressible fluid to the ambient environment to regulate the compressible fluid and substantially maintain it at the low pressure. Compressible fluid at low pressure is supplied by the low pressure regulator 76b to low pressure regulator outlet 62a. Low pressure regulator outlet 62a is fluidly connected by tube 62b to T-connection 62c that fluidly connects low pressure reservoir 62d and low pressure manifold inlet tube 62e. Low pressure fluid source 62 further includes low pressure manifold 62f, which is fluidly connected to and supplied with compressible fluid by the low pressure manifold inlet tube 62e. In the illustrated preferred embodiment, the low pressure regulator 76b supplies compressible fluid to regulator outlet 62a at between about one (1) psig and about two (2) psig, and at about one and on-half (1.5) psig for many commercial embodiments.

Employing a back pressure regulator in this embodiment is preferable because it facilitates regulation of pressure spikes experienced in the low pressure fluid source 62 during operation of the device (see discussion below) by venting compressible fluid. However, a variety of regulators may alternatively be employed within the pressure sources, or no regulator(s) provided at all, without departing from the spirit of the present invention.

Returning to FIGS. 3a-b and 4a-b, vacuum pressure source 64 includes upstream vacuum supply 84. Vacuum supply 84 includes compressor 72, compressor outlet 84a (See FIG. 3b) and a T-connection 84b having a pressure release valve 84c. T-connection 84b fluidly connects compressor outlet 84a to tube 84d (see FIG. 3a). Tube 84d supplies vacuum to vacuum pressure regulator 84e which, in turn, is fluidly connected and supplies vacuum at a vacuum pressure to vacuum pressure outlet 64a. In a preferred embodiment, the vacuum pressure regulator 84e supplies vacuum to vacuum pressure outlet 64a at between about negative one (−1) psig and negative two (−2) psig, and at about negative one and one-half (−1.5) psig in many commercial embodiments. Vacuum pressure regulator outlet 64a is fluidly connected by tube 64b to t-connection 64c that fluidly connects vacuum pressure reservoir 64d and vacuum pressure manifold inlet tube 64e. Vacuum pressure source 64 further includes vacuum pressure manifold 64f, which is fluidly connected to and supplied with vacuum pressure by the vacuum pressure manifold inlet tube 64e.

Figure 5A:
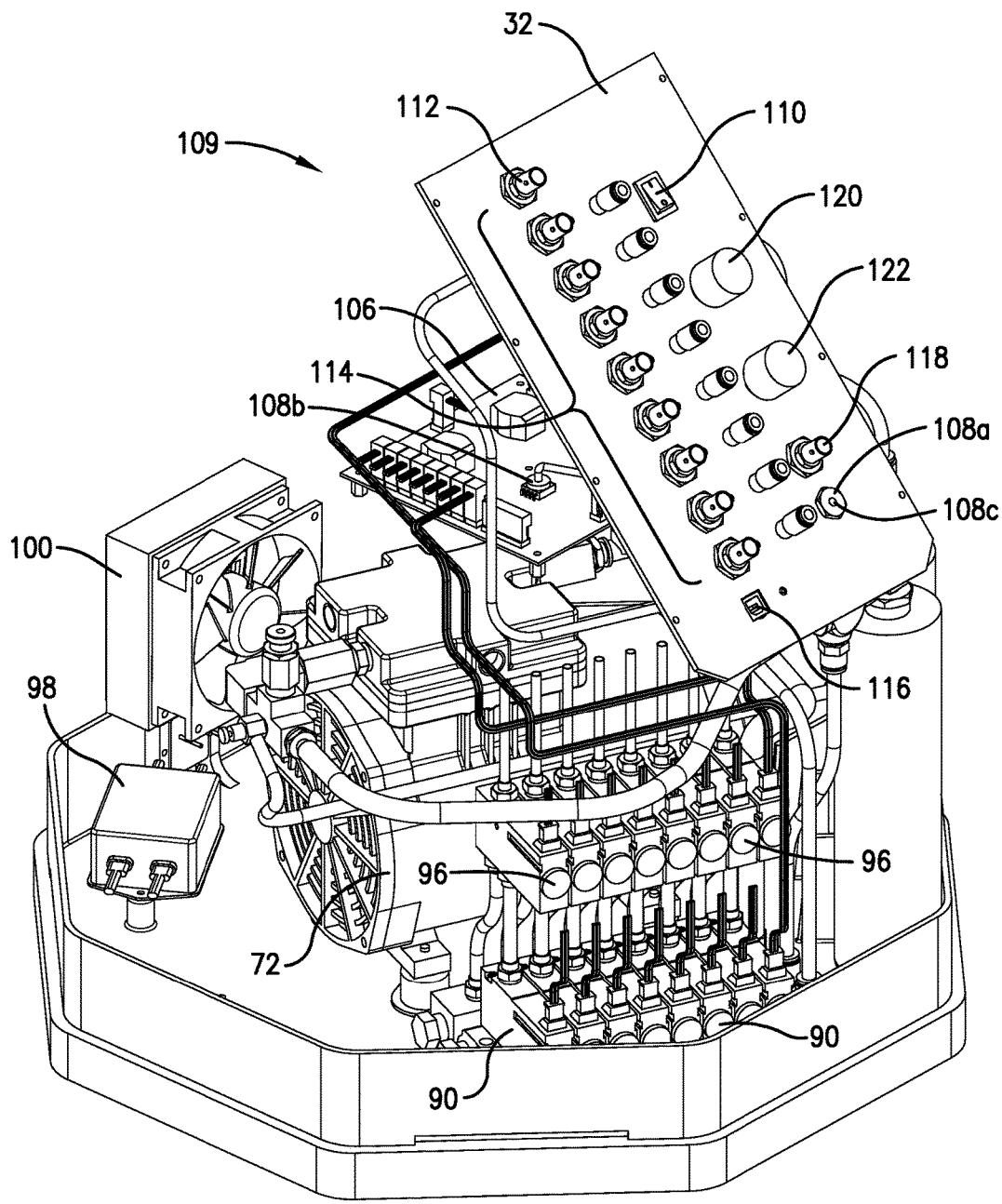
FIG. 5a is a partially sectioned perspective of the device of FIGS. 1-4, with the upper housing section and part of the lower housing section being removed to show the valve and control panel side of the bottom compartment.
Figure 5B:
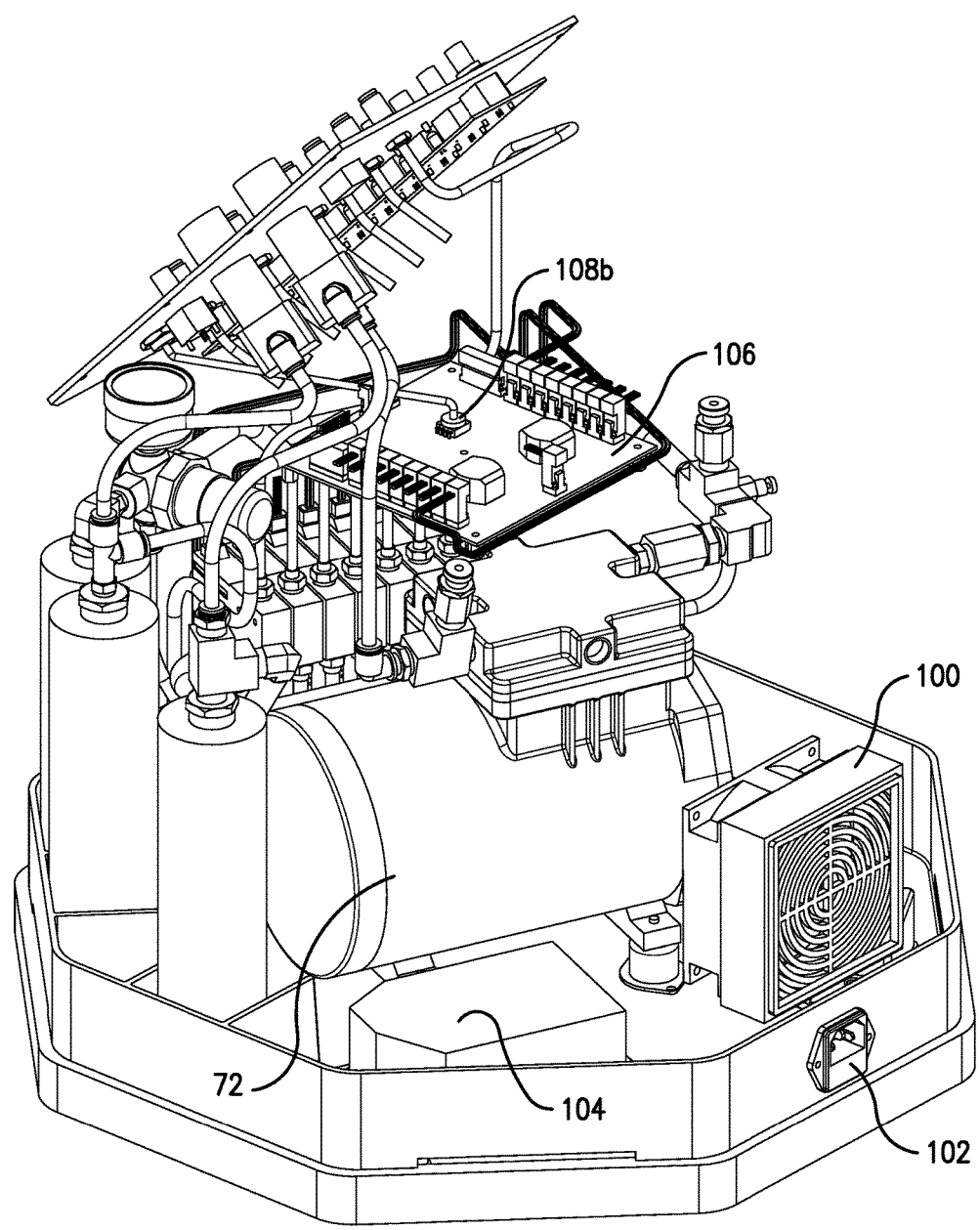
FIG. 5b is a partially sectioned perspective view of the device taken from the opposite angle of FIG. 5a to show the power supply side of the bottom compartment.

As perhaps best shown in FIGS. 5a-b, the compressor 72 preferably provides both the compressor pressure outlet 70a and vacuum outlet 84a. In a preferred embodiment, the compressor 72 is a piston pump operated by an AC motor and is configured to supply compressor pressure outlet 70a with pressurized fluid at about ten (10) psig and the vacuum outlet 84a with a vacuum pressure at between about negative twelve (−12) psig and about negative thirteen (−13) psig. The compressor 72 of the preferred embodiment is configured to utilize ambient air as the compressible fluid. However, it is foreseen that other compressible fluids may be utilized in alternative embodiments according to an assessment of desirable fluid properties such as compressibility, specific heat, friction properties and others, without departing from the spirit of the present invention.

It should be noted that the objective of the components illustrated in the preferred embodiment of FIGS. 3a-b and 4a-b is to supply three pressure sources using an efficient design so that each source may be fluidly connected to each outlet conduit by actuation of one or two fast acting valves. In fact, the availability of at least two pressure sources is critical to the functioning of the preferred embodiment of the present invention. In the preferred embodiment, a high pressure burst is followed as closely as possible by the sustained low pressure carrier wave.

FIGS. 3a-b and 4a-b do, however, merely illustrate a preferred embodiment, and a variety of components for generating, controlling and directing the flow of compressible fluid may be used without departing from the spirit of the present invention. Alternatively put, so long as at least two fluid pressure sources are supplied for selective application to an outlet conduit, various embodiments of the present invention may employ a variety of fluid components known to those of ordinary skill in the art as part of the pressure sources. For example, each manifold of the illustrated preferred embodiment includes a cylindrical chamber (not shown) running beneath and fluidly connected to one set of valves (i.e., pressure valves or vacuum valves, as will be described). However, it is envisioned that other pressure volumes and flow path intermediary components for separating flow to each conduit may be utilized without departing from the spirit of the present invention.

Further, pressure sources may share a common supply, such as the compressor of the preferred embodiment described herein, or may alternatively draw from distinct respective supplies without departing from the spirit of the present invention. Still further, each supply need not comprise a compressor, but may alternatively be other supply volume(s) such as pressurized tanks or the like.

Pressure drop across components that are not primarily configured for manipulating fluid pressure—such as along tube lengths, across valves, and across components having different cross-sectional areas—is a natural consequence of fluid flow. It is anticipated that the preferred embodiment will minimize such natural pressure change(s) as fluid flows within each pressure source. However, appreciable pressure drop is expected as pressure waves travel along an outlet conduit to an applicator in many embodiments. Nonetheless, a single label is used across each flow path to refer to a pressure wave, regardless of possible natural pressure losses occurring along the way. Use of a single label for a pressure wave at two or more points along a flow path—such as referring to the supply of the "high pressure fluid" at the outlet of the corresponding regulator and to the downstream supply of the "high pressure fluid" to an applicator—thus simplifies discussion, without implying the absence of natural pressure changes along path of the wave.

Returning to FIGS. 3a-b and 4a-b, pressure valves 90 are fluidly connected to the high pressure fluid source 60 and the low pressure fluid source 62, and each pressure valve 90 has an outlet 92. Each pressure valve 90 is shiftable to a high pressure position in which the high pressure fluid source 60 is fluidly connected to the outlet 92 for supplying a high pressure burst to an outlet conduit 50. Each pressure valve 90 is also shiftable to a low pressure position in which the low pressure fluid source 62 is fluidly connected to the outlet 92 of the pressure valve 90 for supplying a low pressure carrier wave to the outlet conduit 50. Although not shown, each pressure valve 90 may also be shiftable to an "off" position in which neither the high pressure fluid source 60 nor the low pressure fluid source 62 is fluidly connected to the outlet 92 of the pressure valve 90. Such an alternative configuration is particularly useful, for example, in embodiments where the device is in a parallel configuration (described below), or in embodiments that lack a vacuum valve (see discussion below) or a high or low pressure fluid source.

Figure 4A:
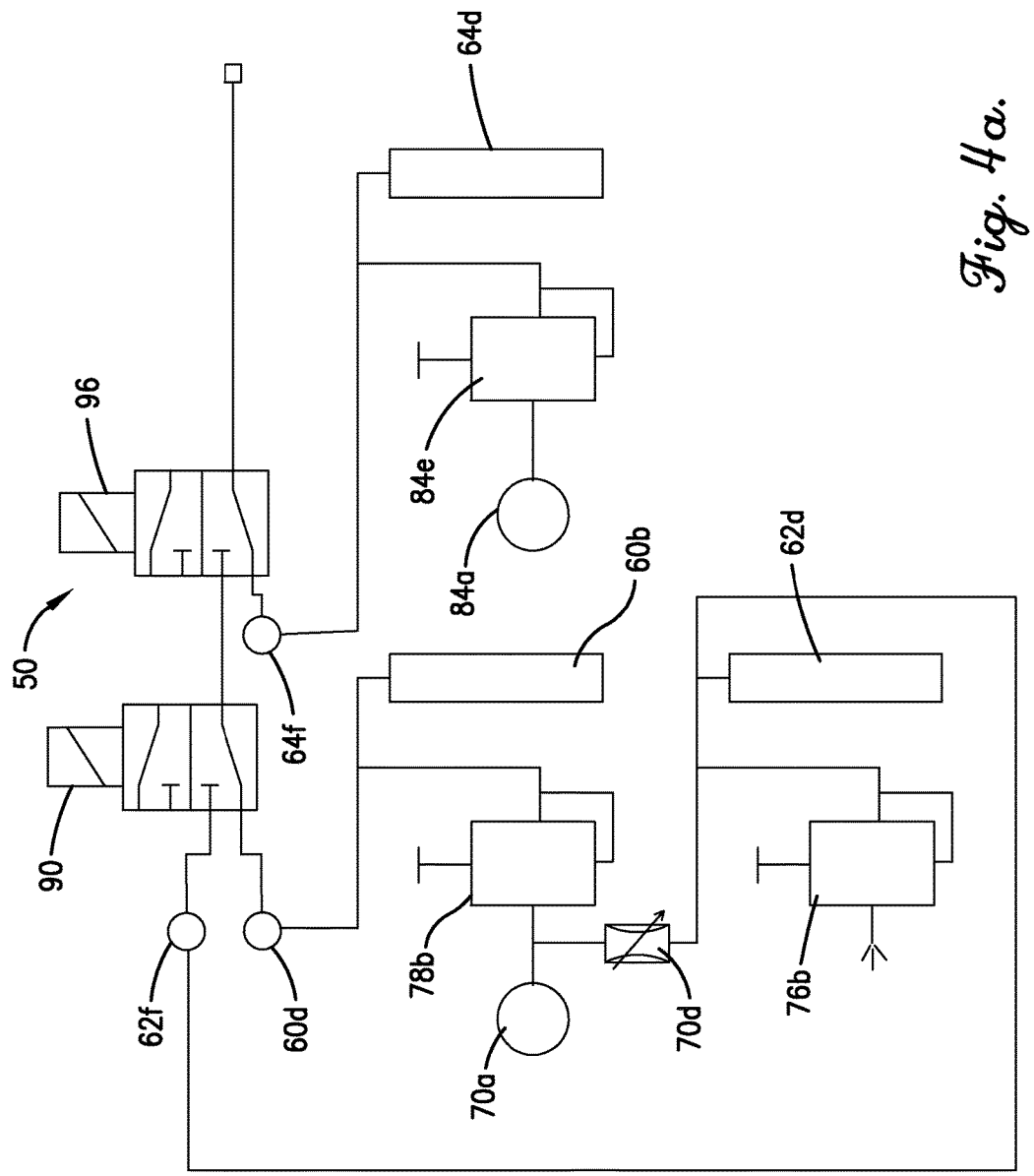
FIG. 4a is a schematic flow diagram of the fluid components of the device of FIGS. 1-3, depicting the device with just one outlet conduit.
Figure 4B:
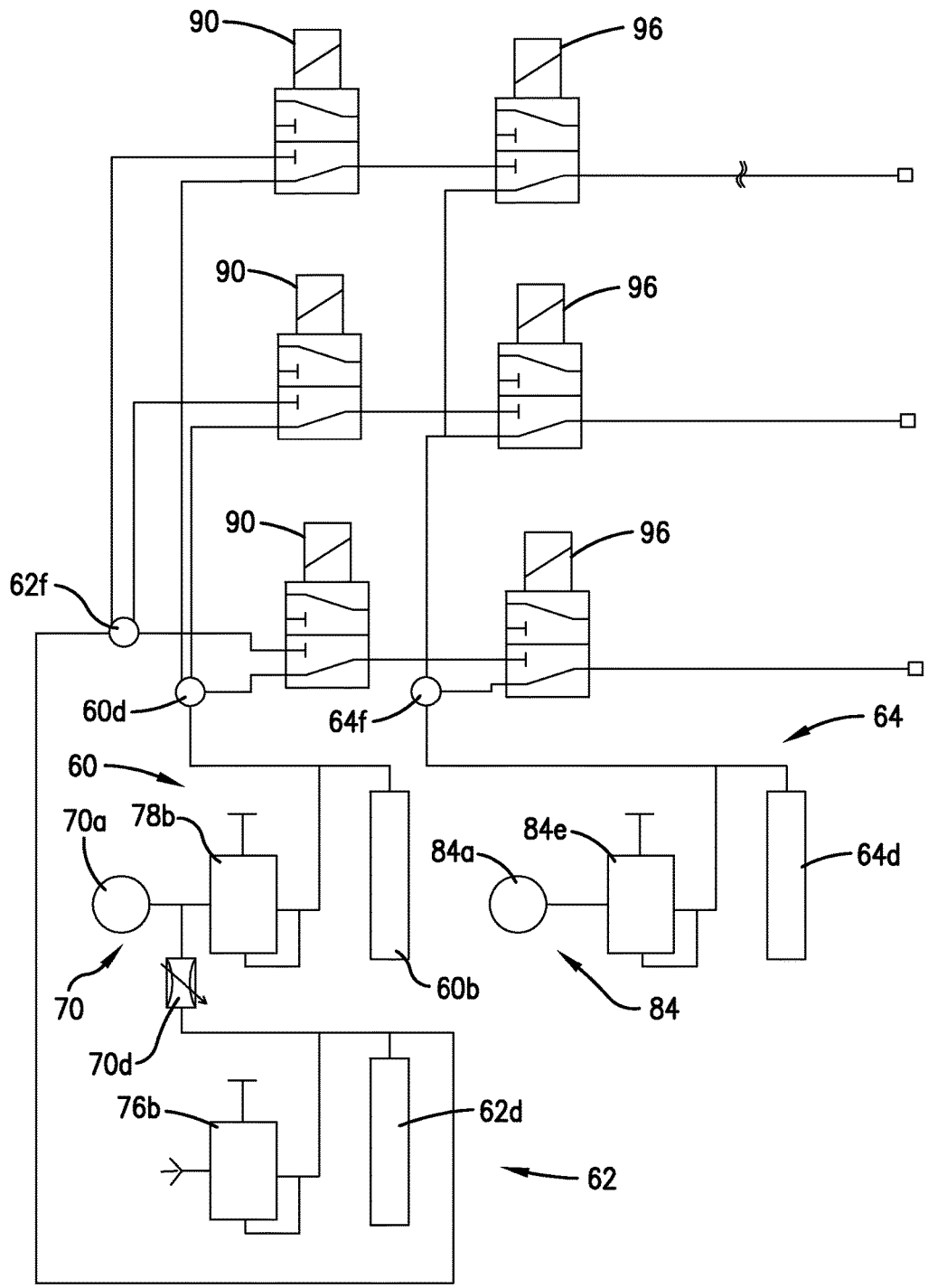
FIG. 4b is a schematic flow diagram of the fluid components of the device of FIGS. 1-4a, depicting the device with three outlet conduits.

In the series configuration illustrated in FIGS. 4a-b, the outlet 92 of each pressure valve 90 is fluidly connected to a corresponding outlet conduit 50. More particularly, a tube 94 extends between and fluidly connects the pressure valve 90 to the corresponding vacuum valve 96. In the preferred embodiment, the tube 94 forms part of the internal section 50c of the outlet conduit 50 and, more preferably, a portion of the relatively rigid portion of the outlet conduit 50. Each vacuum valve 96 is also fluidly connected to the vacuum source 64, and is operable to shift to a pressure or pulse position fluidly connecting the outlet 92 of the pressure valve 90 to the applicator 54. In the illustrated embodiment, the vacuum valve 96 also serves to block flow of fluid from the pressure valve 90 when in the vacuum position, although such a configuration is not required (as will be described). Each vacuum valve 96 is also shiftable to a vacuum position in which the vacuum pressure source 64 is fluidly connected to the outlet conduit 50. Although not shown, each vacuum valve may optionally be shiftable to an "off" position in which no pressure source is fluidly connected to the outlet conduit.

The outlet conduit preferably includes the outlet of the pressure valve and extends to the applicator, though alternative configurations such as those discussed below may also be employed without departing from the spirit of the present invention. In the preferred illustrated embodiment, the outlet 92 begins the internal section 50c of the outlet conduit 50, and vacuum valve 96 is fluidly interposed along and forms part of the internal section 50c. Vacuum valve 96 preferably controls both pressure flow from the pressure valve 90 along the outlet conduit, as well as connection of the vacuum pressure source 64 to the outlet conduit.

The flow paths defined by the pressure valves and vacuum valves are preferably of greater cross-sectional dimension than the minimum inner passageway cross-sectional dimension of the outlet conduit, which may help reduce the resistance to flow presented by the valves. The preferred embodiment employs fast-acting solenoid valves, preferably direct-action valves such as the 153 Series valve sold under the HUMPHREY® trademark and operating in a DC configuration. Such valves are preferably configured to provide a response time of less than about fifteen (15) milliseconds.

FIGS. 5a-b further illustrate the preferred embodiment of the present invention. FIG. 5a illustrates a power filter 98 for reducing electrical noise of the power used by the device 10, a housing cooling structure 100 illustrated as a fan, and an AC power inlet 102 for receipt of a plug for charging and/or powering the device. In alternative embodiments, the device may include a battery (not shown) for powering the device in mobile applications in which AC power supplies are not readily available or positioned advantageously. AC inlet 102 supplies AC power to power supply 104 (see FIG. 5b) and to compressor 72. Preferably, power supply 104 is a 12-volt DC power supply. Power supply 104 in turn supplies power to cooling structure 100 and to valves 90, 96. Power supply 104 also supplies DC power to a 5-volt DC logic power supply (not shown) seated on an internal control board 106. The logic power supply powers logical components of the internal control board 106.

The device 10 of the preferred embodiment further includes an outlet pressure sensor assembly 108 for measuring the pressure of the pulse supplied to the associated applicator 54. The illustrated assembly 108 includes a port 108a and a pressure sensor 108b fluidly connected to the port 108a. The port 108a presents a coupling surface 108c configured to flushly receive the annular lip 54a of the applicator 54, such that the pulse delivered to the applicator 54 is communicated to the sensor 108b.

FIGS. 5a-b also illustrate a control system 109 including a processor or processing element (not shown) and a memory or memory element (not shown), each of which is seated on the internal control board 106. Though not required, in the preferred embodiment of FIG. 1a, the control system 109 further includes an external second processor and memory element (not shown) housed within computer 14. Alternative embodiments may include additional internal and/or external processing or memory elements according to various optimizations of the device.

Each processing element may include processors, microprocessors, microcontrollers, digital signal processors (DSPs), field-programmable gate arrays (FPGAs), analog and/or digital application-specific integrated circuits (ASICs), or the like, or combinations thereof. Each processing element may generally execute, process, or run instructions, code, code segments, software, firmware, programs, applications, apps, processes, services, daemons, or the like. Each processing element may also include hardware components such as finite-state machines, sequential and combinational logic, and other electronic circuits that can perform the functions necessary for the operation of the current invention. Each processing element may be in communication with the other electronic components through serial or parallel links that include address busses, data busses, control lines, and the like.

Each memory element may include data storage components such as read-only memory (ROM), programmable ROM, erasable programmable ROM, random-access memory (RAM) such as static RAM (SRAM) or dynamic RAM (DRAM), hard disks, floppy disks, optical disks, flash memory, thumb drives, universal serial bus (USB) drives, or the like, or combinations thereof. Each memory element may include, or may constitute, a "computer-readable medium". Each memory element may store the instructions, code, code segments, software, firmware, programs, applications, apps, services, daemons, or the like that are executed by the processing element. Each memory element may also store settings, data, documents, sound files, photographs, movies, images, databases, and the like. Any or all of the predetermined values discussed herein, including the predetermined high pressure predetermined amount of time, the second predetermined amount of time, objectives and the frequency of pulses may be stored in one or more memories, such as electrically erasable read-only memories, that are accessible to one or more of the processing elements of the control system.

The control system 109 further includes a power on/off switch 110 seated on the control panel 32, which controls the overall availability of power to the device 10, for example by permitting or cutting off power to the power supply 104. The control system 109 also includes an all channel data output port 112 for exporting data regarding operating conditions and performance of all outlet conduits 50. Yet further, the control system 109 preferably includes eight individual data output ports 114, one each for exporting such data regarding a single outlet conduit 50. The preferred control system 109 additionally includes a common computer port 116, such as a USB port, and an input signal port 118 for receiving instructions electronically. Also, depicted in FIG. 5a are vacuum pressure regulator control knob 120 and low pressure regulator control knob 122.

The data output ports 112, 114, common computer port 116, and input signal port 118 are configured to provide electrical communication between the control system 109 elements housed within or fixed to the mobile housing 20 (described above) and an external processing element such as the processing element found in the laptop computer 14 illustrated in FIG. 1.

The external processing element may receive data regarding the performance and operating conditions of the device 10, such as valve actuation times, effected pulse waveforms from outlet conduits 50, pressure of the compressible fluid at various points in the device 10, set points for controlling the various device components, and other data gathered by the control system 109 relating to device settings and performance history. The external processing element may also be electrically connected to sensing device 12 (see discussion above and FIG. 1) and may receive data from the sensing device 12.

In the illustrated preferred embodiment, the control system 109 is electrically connected and sends signals to the pressure valves 90 and vacuum valves 96 to actuate them and shift their respective positions. The computer 14 preferably provides instructions to the processor of the internal control board 106 regarding device 10 settings and operation, including with respect to valve 90, 96 actuation timing. The processor of the internal control board 106 in this embodiment issues electrical signals to actuate the valves 90, 96 according to the computer 14 instructions.

In the preferred embodiment, the processor of the computer 14 is also electrically connected to the sensing device 12, and receives data therefrom. The preferred control system 109 also optionally provides operational instructions to the sensing device 12 and to the tactile stimulation device 10, although only control of the tactile stimulation device is critical in this embodiment. Moreover, in certain embodiments, the external computer is not required, and the operational instructions for device settings and operation may be generated and issued by the processing element of the internal control board.

The preferred control system 109 may generate operational instructions, which may include adjustments to high pressure, low pressure, vacuum pressure or valve actuation timing with respect to the tactile stimulation device 10, by processing data from the tactile stimulation device 10 and data received from the sensing device 12. Such processing may be done further in view of at least one objective provided by an operator and/or by code stored in memory accessible to the external processing element. For example, an objective may relate to levels of neuronal response sensed by the sensing device 12. If the desired neuronal response is not detected following a pulse, the external processing element of the computer 14 may process this data in conjunction with data regarding the operating parameters of the tactile stimulation device 10, and provide instructions to the internal control board 106 to adjust the operating parameters of the tactile stimulation device 10 in an attempt to generate pulse(s) with a greater chance of fulfilling the desired objective.

In the preferred embodiment, the control system 109 is also electrically connected to and commands the other components of the device 10, for example the compressor 72 to control pressure and vacuum production, the power filter 98, and the housing cooling structure 100 to ventilate or otherwise maintain acceptable temperature within the mobile housing 20.

Returning to FIGS. 4a-b, in one mode of operation in which the device 10 is in the preferred series configuration described above, the device 10 starts from an initial resting state in which the vacuum valve 96 is in the vacuum position fluidly connecting the vacuum pressure source 64 to the outlet conduit 50. In this resting state, the vacuum created by application of the vacuum pressure to the outlet conduit 50 helps to keep the applicator 54 affixed to its application site. In addition, it has been observed that the resulting reduced pressure at the applicator 54 is advantageous in preparing the application site to receive a pulse, and may help optimize neuronal responses to pulse stimuli by creating a greater pressure differential between the resting state and a stimulated state than, for example, that which would be felt if the applicator 54 were at ambient pressure in its resting state. The pressure valve 90 is in a high pressure position in the resting state, fluidly connecting the high pressure fluid source 60 to an inlet (not shown) in the vacuum valve 96, though the vacuum valve 96 has not yet shifted to fluidly connect the high pressure fluid source 60 with the applicator 54.

The pressure valve 90 and vacuum valve 96 are actuated to shift between valve positions by the control system 109 of the device. A pulse is initiated by shifting the vacuum valve 96 from its resting state in the vacuum position to the pressure position, thereby substantially cutting off the fluid connection between the vacuum pressure source 64 and the outlet conduit 50 and establishing a fluid connection between the high pressure fluid source 60 and the applicator 54. This generates an initial burst supplied by the high pressure fluid source 60 at a high pressure that propagates at roughly the speed of sound toward the applicator 54.

After a high pressure pre-determined amount of time, the pressure valve 90 is shifted to the low pressure position thereby substantially cutting off the fluid connection between the high pressure fluid source 60 and the outlet conduit 50 and establishing a fluid connection between the low pressure fluid source 62 and the outlet conduit 50. The low pressure fluid source 62 supplies compressible fluid at the low pressure which in turn propagates toward the applicator 54 at roughly the speed of sound, acting as a carrier wave initially for the high pressure burst and then as a sustained pressure wave for the pulse. After a second pre-determined period of time, the vacuum valve 96 is shifted from the pressure position to the vacuum position to substantially cut off the connection of the low pressure fluid source 62 with the applicator 54 and return the device 10 to its resting state. These steps may be repeated for generation of additional pulses by the device 10 and for creation of pulse patterns having a desirable frequency based on the desired application.

In a preferred embodiment of the above configuration, the high pressure pre-determined period of time is less than about thirty (30) milliseconds, and in many cases optimally between about ten (10) milliseconds to about fifteen (15) milliseconds. The second pre-determined period of time in a preferred embodiment is between about ten (10) milliseconds and about ninety (90) milliseconds. In applications where a pattern of pulses is desired, the time between pulses, i.e., the time in which the device is in a resting state with vacuum pressure applied to the outlet conduit, is preferably between about two-hundred (200) milliseconds and about one thousand (1000) milliseconds.

It should be noted that, in the illustrated preferred embodiment, the tube 94 connecting pressure valve 90 to vacuum valve 96 may dump residual high pressure compressible fluid into the low pressure fluid source 62 following shifting of the pressure valve 90 from the high pressure position to the low pressure position. This is one of the pressure spike scenarios described above in which the low pressure regulator 76b comprising a back pressure regulator is particularly useful in bleeding off such excess high pressure from the low pressure fluid source.

Reference to a high, low or vacuum pressure associated with one of the regulator outlets does not necessarily indicate the direction of flow of compressible fluid is away from such outlet. This is particularly true in the case of vacuum pressure or in instances of flow to the low pressure regulator, wherein the fluid moves toward (not away) from the regulator. For example, the low pressure regulator will commonly regulate the low pressure supplied by the pressurized fluid supply by releasing higher pressure compressible fluid to the ambient environment (see discussion above of back pressure regulator). In these embodiments, higher pressure fluid flows toward the low pressure regulator for partial venting to regulate the low pressure fluid, even though the low pressure regulator is said to be "supplying" the low pressure fluid. In another example, where a high pressure spike occurs "downstream" in the low pressure fluid source during operation, such as at the pressure valve in the pressurized series configuration, fluid pressure may actually flow from the low pressure manifold "upstream" through the manifold inlet tube and up through other components of the low pressure fluid source until the spike is vented by the low pressure regulator to return the low pressure fluid source to the target low pressure. In certain embodiments, the effects of any such pressure spikes may be minimized by reducing the volume of the fluid connection between the pressure valve and vacuum valve and/or by increasing the volume of the low pressure reservoir. In a further example, the vacuum pressure source normally supplies a vacuum to the outlet conduit, thus drawing compressible fluid flow toward the vacuum pressure regulator.

Through the series of steps outlined above, the preferred embodiment of the tactile stimulation device 10 generates two-stage pulses of compressible fluid—comprising a high pressure burst backed by a low pressure carrier wave—directed to an application site by an applicator 54. This new two-stage pulse has advantages that are desirable for a wide range of medical uses, including diagnostic and therapeutic applications. The two-stage pulse of embodiments of the present invention improves sluggish rise times and imprecise wave forms of prior art devices, thereby permitting creation of, for example, more "rectangular" waveforms such as those previously only realized by tactile stimulation devices relying on electrical current to carry pulses to the subject.

For example, prior art devices may employ fluid lines about fifteen (15) feet in length to carry pulses of compressible fluid from a compressor to an application site. With the prior art device, each exemplary pulse may be initiated by turning the compressor on and concluded by turning the compressor off, for application of a pulse of about fifty (50) milliseconds to an application site of a person. Typical stimulus rise times—defined as the time it takes for the stimulus to progress from ten percent (10%) to ninety percent (90%) of its peak intended amplitude—are considered very rapid in prior art devices at around twenty-five (25) milliseconds. Given that an exemplary pulse lasts for around fifty (50) milliseconds, the pulse of prior art devices is commonly delivered in a relatively parabolic waveform at the application site near the skin.

By employing the two-stage pulse of the preferred embodiment of the present invention, shorter rise times are achievable, such that the largely parabolic pulse waveforms of existing devices may be replaced with more "rectangular" waveforms. In many cases, this permits much more of the duration of each pulse to be held at the desired pulse pressure or stimulus amplitude rather than, for example, merely being applied at the peak of a parabolic waveform pulse. The device 10 supplies better waveforms while also providing a relatively cheap solution that does not require positioning of pressure sources that are likely to interfere with sensory equipment operation.

Further, the waveform produced by the device 10 may be observed, and the device may be tuned for each individual outlet conduit in consideration of the application and objectives being sought after. This also permits optimization for each unique outlet conduit in view of possible variance of physical properties and imperfections that may be or become apparent from one conduit/valve passage to the next. Exemplary imperfections may include small variations in actuation timing between valves and the like.

For example, as described elsewhere herein "rectangular" waveforms are preferred for certain applications such as in diagnostic somatosensory testing, and it has been observed that a rise time of fifteen (15) milliseconds or less may be advantageous in such applications. An operator of the device 10 may tune each outlet conduit 50 individually according to these exemplary objectives by first coupling the applicator 54 to the port 108a at the control panel 32. The operator may then initiate generation of a pulse according to the description above, and record the resulting waveform via output of the sensor 108b. If the rise time is seventeen (17) milliseconds, for example, the operator may wish to increase the high pressure pre-determined period of time to decrease rise time. Such an adjustment, may, however, also increase "overshoot"—the front part of a pulse waveform that exceeds the target pulse pressure before falling back to the desired pressure. Other variables that may be useful for tuning include high pressure, low pressure, and, in more experimental settings, outlet conduit length and inner diameter, tube bore smoothness, applicator dimensions, and the like.

By way of more specific example, where predetermined periods of time are measured to properly coordinate pulses and pulse stages, in a preferred embodiment, time measuring commences upon the shifting of a valve position, and more particularly when the corresponding actuation signal is issued by the control system 109. However, actuation times may vary across valves. Thus, to achieve a pressure flow of a desired duration, it may be necessary to perform additional tuning to account for any such inconsistencies. An example based on the device 10 of the preferred embodiment may comprise the following sequence of events: (a) send electrical signal for actuation of the vacuum valve 96 to the pressure position, commencing the high pressure pre-determined amount of time, (b) after passage of the high pressure pre-determined amount of time, for example fifteen (15) milliseconds, send electrical signal for actuation of the pressure valve 90 to the low pressure position, commencing the second pre-determined period of time, and (c) after passage of the second pre-determined period of time, for example thirty-five (35) milliseconds, send electrical signal for actuation of the vacuum valve 96 to the vacuum position, returning the device 10 to the resting state. If, following this sequence and measurement of the resulting pulse by the outlet pressure sensor assembly 108, it is determined that either of the high pressure burst or low pressure carrier wave does not achieve the duration expected had the valves performed their positional shifts in substantially the same amount of time, the device may be tuned by adjusting the timing commanded by the control system 109 to achieve the desired waveform and characteristics.

Individual tuning and the ability to actuate pulses independently along separate outlet conduits permits patterns of pulses to be fashioned, for example to simulate stroking touches or the like. The embodiment of FIG. 1a illustrates such a pattern arrangement. The eight outlet conduits 50 extend toward the subject in two groups of four, with one group applied to the left arm and the other to the right arm in linear application site patterns. Exemplary pulse patterns that may be supplied to the applicators 54 of each group in this arrangement include a stroking pattern simulated by applying a pulse to each of the four applicators 54 in a closely-timed successive series. More specifically, a pulse may be delivered to a first applicator 54 of the left arm group, a second pulse may be delivered just after the first pulse to the next applicator 54 in the illustrated linear configuration, followed in quick succession by a pulse each for the third and fourth applicators 54. This pattern results in simulation of a stroking motion quickly moving up the left arm from the first applicator 54 to the fourth applicator 54. A similar pattern may be applied simultaneously or with staggered timing by the right arm group of applicators 54. It is envisioned that other application site patterns, pulse patterns, and pulse frequencies may be employed with embodiments of the device of the present invention without departing from its spirit.

Though the pressure sensor port is preferably mounted on the control panel, it is also foreseen that tuning may be achieved by a variety of other means such as by including an applicator pressure sensor at each applicator and by optionally providing a feedback loop from each applicator pressure sensor to a processor that analyzes the feedback data and automatically adjusts system settings according to a waveform optimization objective such as the desired rise time and maximum overshoot definition.

The present invention provides advantages over the prior art, including that it provides improved tactile stimulation using a pneumatic device for delivering pulses of compressible fluid over a distance so that sluggish rise time, imprecise waveforms and other disadvantages of existing pneumatic tactile stimulation devices can be minimized. In one implementation, the present invention accomplishes this with a less complex and less expensive solution that does not, for example, require positioning of pressure sources that are likely to interfere with sensory equipment operation.

As discussed above, the outlet conduit preferably includes the outlet of the pressure valve and extends to the applicator, and includes a vacuum valve. However, alternative configurations may also be employed without departing from the spirit of the present invention. In another embodiment illustrated in FIG. 6, the pressure valve 200 has an outlet 202 fluidly connected to the applicator 204, and the vacuum valve 206 is not fluidly interposed there between. The vacuum valve 206 in this configuration is fluidly connected to the outlet conduit 208 to supply vacuum pressure thereto, for example at a t-connection with the outlet conduit 208. In this parallel configuration, pressure valve 200 and vacuum valve 206 are preferably shiftable to an "off" position. In the illustrated embodiment, pressure valve 200 is shown as a three position valve, which is an exemplary mechanism for providing the "off" functionality for the pressure valve 200.

Figure 6:
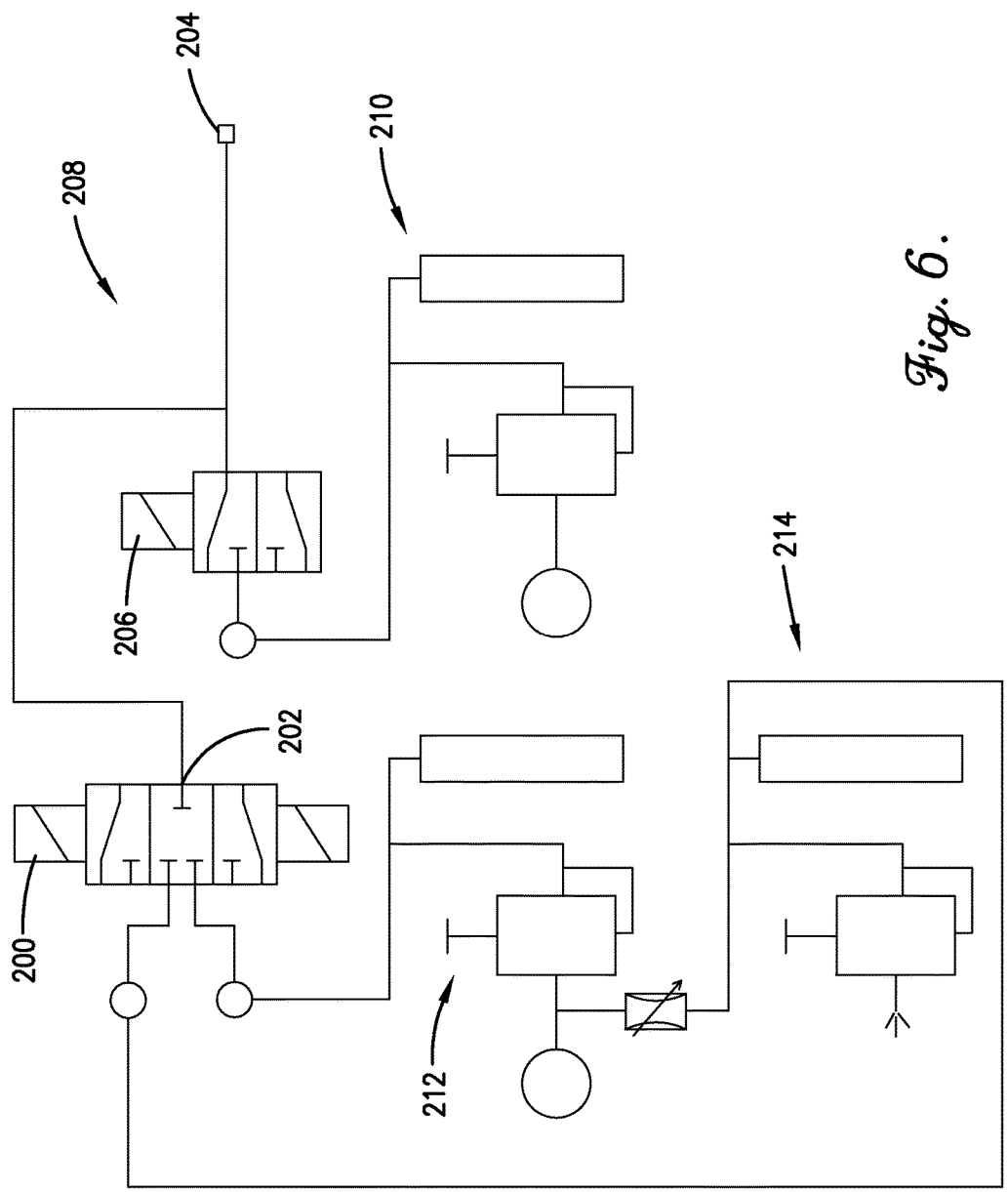
FIG. 6 is a schematic flow diagram of the fluid components of a device constructed in accordance with a second embodiment of the present invention, with the device having one outlet conduit.

In the resting state of the parallel configuration illustrated in FIG. 6, the pressure valve 200 is in its "off" position as described above and the vacuum valve 206 is in its vacuum position fluidly connecting the vacuum source 210 to the outlet conduit 208. A pulse is initiated for the applicator 204 by shifting the vacuum valve 206 from its resting state in vacuum position to its "off" position, thereby substantially cutting off the fluid connection between the vacuum pressure source 210 and the outlet conduit 208. As closely thereafter as possible, or simultaneously, the pressure valve 200 is shifted to the high pressure position, thereby establishing a fluid connection between the high pressure fluid source 212 and the outlet conduit 208. This generates an initial burst supplied by the high pressure fluid source 212 at a high pressure that propagates at roughly the speed of sound toward the applicator 204.

After a high pressure pre-determined amount of time, the pressure valve 200 is shifted to the low pressure position thereby substantially cutting of the fluid connection between the high pressure fluid source 212 and the outlet conduit 208 and establishing a fluid connection between the low pressure fluid source 214 and the outlet conduit 208. The low pressure fluid source 214 supplies compressible fluid at the low pressure which in turn propagates toward the applicator 204 at roughly the speed of sound, acting as a carrier wave initially for the high pressure burst and then as a sustained pressure wave for the pulse. After a second pre-determined period of time, the pressure valve 200 is shifted back to the "off" position to substantially cut off the fluid connection between the low pressure fluid source 214 and the outlet conduit 208. The vacuum valve 206 is shifted as soon thereafter as possible, or simultaneously, from the "off" position to the vacuum position to return the device to its resting state.

In a preferred embodiment of the above parallel configuration, the high pressure pre-determined period of time is between about ten (10) milliseconds and about thirty (30) milliseconds, and in many cases optimally between about ten (10) milliseconds to about fifteen (15) milliseconds. The second pre-determined period of time in a preferred embodiment is between about ten (10) milliseconds and about ninety (90) milliseconds. In applications where a pattern of pulses is desired, the time between pulses, i.e., the time in which the device is in a resting state with vacuum pressure applied to the outlet conduit, of a preferred embodiment is between about two hundred (200) milliseconds and about one thousand (1000) milliseconds.

It should be noted, for example with respect to the three position valve 200 illustrated in FIG. 6, that a multi-position valve described herein may be replaced with a plurality of valves connected in parallel, without departing from the spirit of the present invention.

In a third embodiment of the present invention (not shown), the vacuum valve may be removed from the outlet conduit. In the resting state of this third embodiment, the pressure valve is in its "off" position. A pulse is initiated for the outlet conduit by shifting the pressure valve from its "off" position to the high pressure position thereby establishing a fluid connection between the high pressure fluid source and the outlet conduit. This generates an initial burst supplied by the high pressure fluid source at a high pressure that propagates at roughly the speed of sound toward the applicator. After a high pressure pre-determined amount of time, the pressure valve is shifted to the low pressure position thereby substantially cutting of the fluid connection between the high pressure fluid source and the outlet conduit and establishing a fluid connection between the low pressure fluid source and the outlet conduit. The low pressure fluid source supplies compressible fluid at the low pressure which in turn propagates toward the applicator at roughly the speed of sound, acting as a carrier wave initially for the high pressure burst and then as a sustained pressure wave for the pulse. After a second pre-determined period of time, the pressure valve is shifted back to the "off" position to substantially cut off the fluid connection between the low pressure fluid source and the outlet conduit.

In a fourth embodiment of the present invention (not shown), the vacuum valve is fluidly connected to a pressure source as well as to the vacuum source. In one embodiment, this may be accomplished by removing the tube 94 illustrated as running between pressure valve and the vacuum valve in FIG. 3a from the outlet 92 of the pressure valve 90 and fluidly connecting it directly to one of the manifolds 20d and 30f. If this fourth embodiment, the outlet conduit extends from the vacuum valve outlet to the applicator. The vacuum valve is shiftable between a pressure position fluidly connecting such pressure fluid source to the applicator, and a vacuum position fluidly connecting the vacuum pressure source to applicator. A pulse is initiated by shifting from the vacuum position to the pressure position for a pressure pre-determined period of time, and is concluded by shifting back to the vacuum position. Preferably, in this fourth embodiment the pressure pre-determined period of time is between about forty (40) milliseconds and about one hundred (100) milliseconds. In applications where a pattern of pulses is desired, the time between pulses, i.e., the time in which the device is in a resting state with vacuum pressure applied to the outlet conduit, of a preferred embodiment is between about two-hundred (200) milliseconds and about one thousand (1000) milliseconds.

Although the above description presents features of preferred embodiments of the present invention, other preferred embodiments may also be created in keeping with the principles of the invention. Furthermore, these other preferred embodiments may in some instances be realized through a combination of features compatible for use together despite having been presented independently in the above description.

The preferred forms of the invention described above are to be used as illustration only and should not be utilized in a limiting sense in interpreting the scope of the present invention. Obvious modifications to the exemplary embodiments, as hereinabove set forth, could be readily made by those skilled in the art without departing from the spirit of the present invention.

For the avoidance of doubt, reference to "each" component, for example to "each valve," in describing the exemplary embodiments disclosed herein does not imply a requirement that a certain minimum number of outlet conduits or valves be included in the present invention other than as expressly stated in any claims, nor that each outlet conduit/valve pair of a device according to an embodiment of the present invention must operate in the same configuration as others.

The inventors hereby state their intent to rely on the Doctrine of Equivalents to determine and assess the reasonably fair scope of the present invention as pertains to any apparatus not materially departing from but outside the literal scope of the invention set forth in the following claims.

What is claimed is:

1. A device for providing tactile stimulation via a pulse of compressible fluid, said tactile stimulation device comprising:
    a high pressure fluid source;
    a low pressure fluid source;
    an outlet conduit being fluidly connectable to the fluid sources and including an applicator configured to direct the pulse against a first area of skin of a subject;
    a pressure valve fluidly interposed between the applicator and the fluid sources,
    said pressure valve being shiftable between a high pressure position, in which the high pressure fluid source is fluidly connected to the outlet conduit, and a low pressure position, in which the low pressure fluid source is fluidly connected to the outlet conduit, with positioning of the pressure valve in the high pressure position and the low pressure position supplying the pulse of compressible fluid to the applicator;
    a vacuum pressure source; and
    a vacuum valve shiftable between a vacuum position, in which the vacuum pressure source is fluidly connected to the outlet conduit, and a pulse position, in which the vacuum pressure source is not fluidly connected to the outlet conduit.

2. The tactile stimulation device as claimed in claim 1, wherein:
said low pressure fluid source supplies fluid at a pressure above ambient pressure,
said high pressure fluid source supplies fluid at a pressure above that of the low pressure fluid source.

3. The tactile stimulation device as claimed in claim 1, further comprising:
a control system operably coupled to the valves to control shifting of the valves between their respective positions.

4. The tactile stimulation device as claimed in claim 3, said control system including a first processor electrically connected to the pressure valve, wherein the first processor is configured to provide electrical signals for triggering shifting of the pressure valve between the high pressure and low pressure positions,
said control system further including a second processor configured to provide instructions to the first processor.

5. The tactile stimulation device as claimed in claim 3, further comprising:
a data link coupled to the control system and being connectable to a neuronal sensing device.

6. The tactile stimulation device as claimed in claim 3, said control system being operable to initially position the vacuum valve in the vacuum position while fluid flow from the pressure valve is blocked, and then shift the vacuum valve to the pulse position,
said control system being operable to position the pressure valve in the high pressure position and, after a high pressure predetermined amount of time, shift the pressure valve to the low pressure position.

7. The tactile stimulation device as claimed in claim 6, further comprising:
an outlet pressure sensor connectable to the applicator to sense a pressure associated with the pulse supplied to the applicator,
said outlet pressure sensor being operably coupled with the control system.

8. The tactile stimulation device as claimed in claim 6, said vacuum valve being fluidly interposed along the outlet conduit between the pressure valve and the applicator,
said vacuum valve fluidly connecting the pressure valve to the applicator when in the pulse position,
said vacuum valve blocking fluid flow from the pressure valve when in the vacuum position, such that shifting of the vacuum valve from the vacuum position to the pulse position permits the pulse of compressible fluid to propagate toward the applicator.

9. The tactile stimulation device as claimed in claim 8, said control system being operable to initially position the pressure valve in the high pressure position and the vacuum valve in the vacuum position,
said control system being operable to maintain the pressure valve in the high pressure position while the vacuum valve is shifted to the pulse position, with the high pressure predetermined amount of time commencing when the vacuum valve is shifted to the pulse position.

10. The tactile stimulation device as claimed in claim 9, said control system being operable to return the vacuum valve back to the vacuum position after a second predetermined amount of time, with the second predetermined amount of time commencing once the high pressure predetermined amount of time expires.

11. The tactile stimulation device as claimed in claim 10, said high pressure predetermined amount of time being nonzero and equal to or less than 30 milliseconds,
said second predetermined amount of time being between 10 milliseconds and 90 milliseconds, inclusive.

12. The tactile stimulation device as claimed in claim 11, said high pressure predetermined amount of time being between 10 milliseconds and 15 milliseconds, inclusive.

13. The tactile stimulation device as claimed in claim 1, said high pressure fluid source being operable to supply compressible fluid at a pressure between 6 psig and 10 psig, inclusive,
said low pressure fluid source being operable to supply compressible fluid at a pressure between 1 psig and 2 psig, inclusive,
said vacuum pressure source being operable to supply a vacuum between −1 psig and −2 psig, inclusive.

14. The tactile stimulation device as claimed in claim 1, each of said valves being a fast-acting solenoid valve configured to complete shifting between the respective valve positions in a nonzero time period less than or equal to 15 milliseconds.

15. The tactile stimulation device as claimed in claim 1, said outlet conduit defining an inner conduit flow passageway having a minimum passageway cross-sectional dimension,
said pressure valve defining an inner valve flow path having a minimum path cross-sectional dimension that is greater than the passageway cross-sectional dimension.

16. The tactile stimulation device as claimed in claim 15, said minimum passageway cross-sectional dimension being between 0.002 square inches and 0.05 square inches, inclusive.

17. The tactile stimulation device as claimed in claim 1, said outlet conduit including proximal and distal sections, with the proximal section being adjacent the pressure valve and the distal section being adjacent the applicator,
said distal section being more flexible than the proximal section.

18. The tactile stimulation device as claimed in claim 1, each of said pressure sources comprising a regulator and a reservoir positioned upstream from the regulator.

19. The tactile stimulation device as claimed in claim 18, said pressure sources including a common fluid compressor supplying pressurized fluid to both of the reservoirs.

20. The tactile stimulation device as claimed in claim 1, further comprising:
a second outlet conduit being fluidly connectable to the fluid sources and including a second applicator configured to direct a second pulse against a second area of the skin of the subject; and
a second pressure valve fluidly interposed between the second applicator and the fluid sources,
said second pressure valve being shiftable between a first position fluidly connecting the high pressure fluid source to the second outlet conduit and a second position fluidly connecting the low pressure fluid source to the second outlet conduit, wherein shifting the second pressure valve from the first position to the second position supplies a second pulse of compressible fluid to the second applicator.

21. The tactile stimulation device as claimed in claim 1, further comprising:
a mobile housing in which the fluid sources and the pressure valve are located, said outlet conduit extending from the mobile housing to the subject.

22. The tactile stimulation device as claimed in claim 21, said outlet conduit presenting a length between 3 feet and 30 feet, inclusive, with at least a majority of the length of the outlet conduit being external to the mobile housing.

* * * * *